United States Patent
Hailman et al.

(10) Patent No.: US 11,407,825 B2
(45) Date of Patent: Aug. 9, 2022

(54) NAPI2B-TARGETED POLYMER ANTIBODY-DRUG CONJUGATES AND METHODS OF USE THEREOF

(71) Applicant: Mersana Therapeutics, Inc., Cambridge, MA (US)

(72) Inventors: Eric P. Hailman, Lexington, MA (US); Donna M. Jarlenski, New Haven, CT (US); Donald A. Bergstrom, Winchester, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 214 days.

(21) Appl. No.: 16/542,642

(22) Filed: Aug. 16, 2019

(65) Prior Publication Data

US 2020/0055933 A1    Feb. 20, 2020

Related U.S. Application Data

(60) Provisional application No. 62/854,701, filed on May 30, 2019, provisional application No. 62/808,376, filed on Feb. 21, 2019, provisional application No. 62/733,380, filed on Sep. 19, 2018, provisional application No. 62/719,189, filed on Aug. 17, 2018.

(51) Int. Cl.
| | | |
|---|---|---|
| *C07K 16/28* | (2006.01) | |
| *A61K 47/68* | (2017.01) | |
| *A61P 35/00* | (2006.01) | |
| *A61K 9/00* | (2006.01) | |

(52) U.S. Cl.
CPC .......... *C07K 16/28* (2013.01); *A61K 47/6883* (2017.08); *A61P 35/00* (2018.01); *A61K 9/0019* (2013.01)

(58) Field of Classification Search
CPC .. C07K 16/28; A61K 47/6883; A61K 9/0019; A61K 47/59; A61K 47/6851; A61K 47/6869; A61K 47/6803; A61K 47/6857; A61K 2039/505; A61P 35/00
See application file for complete search history.

(56) References Cited

U.S. PATENT DOCUMENTS

| | | |
|---|---|---|
| 4,816,567 A | 3/1989 | Cabilly et al. |
| 5,585,089 A | 12/1996 | Queen et al. |
| 5,614,367 A | 3/1997 | Kaluza |
| 7,803,562 B2 | 9/2010 | Cannon et al. |
| 8,383,799 B2 | 2/2013 | Guo et al. |
| 8,535,675 B2 | 9/2013 | Dennis et al. |
| 8,603,474 B2 | 12/2013 | Ritter et al. |
| 8,703,714 B2 | 4/2014 | Doronina et al. |
| 8,742,076 B2 | 6/2014 | Cohen et al. |
| 8,802,094 B2 | 8/2014 | Cook et al. |
| 8,809,339 B2 | 8/2014 | Lewis et al. |
| 8,815,908 B2 | 8/2014 | Lewis et al. |
| 8,815,910 B2 | 8/2014 | Lewis et al. |
| 8,900,589 B2 | 12/2014 | Beria et al. |
| 8,916,569 B2 | 12/2014 | Lewis et al. |
| 9,045,533 B2 | 6/2015 | Ritter et al. |
| 10,947,317 B2 * | 3/2021 | Bergstrom ......... A61K 47/6811 |
| 2003/0039649 A1 | 2/2003 | Foote |
| 2012/0321583 A1 | 12/2012 | Kiy et al. |
| 2015/0104407 A1 * | 4/2015 | Yurkovetskiy ..... A61K 47/6883 424/78.3 |
| 2017/0266311 A1 | 9/2017 | Bergstrom et al. |
| 2019/0160181 A1 | 5/2019 | Mosher et al. |
| 2021/0301031 A1 | 9/2021 | Bergstrom et al. |

FOREIGN PATENT DOCUMENTS

| | | | |
|---|---|---|---|
| CN | 103747804 A | 4/2014 | |
| EP | 2 423 232 A1 | 2/2012 | |
| JP | 2013-511993 A | 4/2013 | |
| WO | WO 2003/060086 A2 | 7/2003 | |
| WO | WO 2009/097128 A1 | 8/2009 | |
| WO | WO 2011/066503 A2 | 6/2011 | |
| WO | WO 2012/171020 A1 | 12/2012 | |
| WO | WO 2015/054669 A1 | 4/2015 | |
| WO | WO 2017/068097 A1 | 4/2017 | |
| WO | WO 2017/160753 A1 | 9/2017 | |
| WO | WO 2017/160754 A1 | 9/2017 | |
| WO | WO-2017160754 A1 * | 9/2017 | ......... A61K 47/6869 |
| WO | WO 2018/237262 A1 | 12/2018 | |

OTHER PUBLICATIONS

Kunik, et al., PLoS Computational Biology, Feb. 2012, vol. 8, Issue 2 (Year: 2012).*
Mersana Therapeutics (Clinical Trial. Identifier: NCT03319628. First Posted Oct. 24, 2017) (Year: 2017).*
Kim, et al., The Korean Journal of Internal Medicine. vol. 25, No. 4, Dec. 2010) (Year: 2010).*
The Human Protein Atlas (https://v15.proteinatlas.org/ENSG00000157765-SLC34A2/cancer/tissue/endometrial+cancer; Build 12 Dec. 5, 2013) (Year: 2013).*
Fisher, et al., Modern Pathology (2014) 27, 222-230 (Year: 2014).*
Bacus et al. "The Evaluation of Estrogen Receptor in Primary Breast Carcinoma by Computer-Assisted Image Analysis", Am J Clin Pathol. vol. 90, No. 3, p. 233-239, (1988).
Banerjee S. et al. "A Randomized, Open-Label, Phase II Study of Anti-NaPi2b Antibody-Drug Conjugate Lifastuzumab Vedotin (DNIB0600A) Compared to Pegylated Liposomal Doxorubicin in Patients with Platinum-Resistant Ovarian Cancer",ASCO Annual Meeting, Jun. 3-7, 2016, slide 5569,1 page.

(Continued)

*Primary Examiner* — Julie Wu
*Assistant Examiner* — John L Van Druff
(74) *Attorney, Agent, or Firm* — Cooley LLP; Cynthia A. Kozakiewicz; Andrew Henderson

(57) ABSTRACT

Disclose herein are dosing regimens for targeted NaPi2b antibody-drug conjugates for treating cancer.

12 Claims, 8 Drawing Sheets

Specification includes a Sequence Listing.

(56) References Cited

OTHER PUBLICATIONS

Banerjee S., et al. "Anti-NaPi2b antibody-drug conjugate lifastuzumab vedotin (DNIB0600A) compared with pegylated liposomal doxorubicin in patients with platinum-resistant ovarian cancer in randomized, open-label, phase II study," Annals of Oncology, vol. 29, p. 917-923 (2018).
Bodyak, N. et al. "Abstract 1194: Discovery and preclinical development of a highly potent NaPi2btargeted antibody-drug conjugate (ADC) with significant activity in patient-derived non-small cell lung cancer (NSCLC) xenograft models", Mersana Therapeutics (poster), Experimental and Molecular Therapeutics, AACR Journals, 1071h Annual Meeting Apr. 16-20, 2016, vol. 76, Issue 14, p. 1-3 (published 2016).
Bodyak, N. et al. "Discovery and preclinical development of a highly potent NaPi2b-targeted antibody-drug conjugate (ADC) with significant activity in patient-derived non-small cell lung cancer (NSCLC) xenograft models", Mersana Therapeutics (poster), 1 page (2016).
Bodyak et al. "The Dolaflexin-based antibody-drug conjugate XMT-1536 targets the solid tumor lineage antigen SLC34A2/NaPi2b, Mol Cancer Ther, American Association for Cancer Research", Author Manuscript Published OnlineFirst on Mar. 15, 2021, p. 1-27.
Bowie et al., "A method to identify protein sequences that fold into a known three-dimensional structure", Science, vol. 253, p. 164-170 (1991).
Burris, H. et al. "A phase I study of DNIB0600A, an antibody-drug conjugate (ADC) targeting NaPi2b, in patients (pts) with non-small cell lung cancer (NSCLC) or platinum-resistant ovarian cancer (OC)", J Clin Oncol 32, Abstract 2504, p. 1-4 (2014).
Carter et al. "Antibody-Drug Conjugates for Cancer Therapy", The Cancer Journal, vol. 14, No. 3, p. 154-169 (2008).
"Chimeric Antibodies" at https://absoluteantibody.com/our-technology/formats-we-have-made/chimeric-antibodies/, downloaded Jul. 27, 2021, p. 1-6, (2021).
Cerami et al. "The cBio Cancer Genomics Portal: An Open Platform for Exploring Multidimensional Cancer Genomics Data", Cancer Discovery, vol. 2, No. 5, p. 401-404 (2012).
Chothia et al. "Canonical Structures for the Hypervariable Regions of Immunoglobins", J Mol. Biol., vol. 196, p. 901-917 (1987).
Chothia et al. "Conformations of immunoglobulin hypervariable regions", Nature, vol. 342, p. 877-883 (1989).
Chow et al. "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry), vol. 46, p. 72-78 (2001).
Cook, "Use and Misuse of the Receiver Operating Characteristic Curve in Risk Prediction," Circulation, vol. 115, p. 928-935 (2007).
D'Arcangelo, M. et al. "Prevalence and prognostic significance of sodium-dependent phosphate transporter 2b (NaPi2b) protein expression in non-small cell lung cancer", Annals of Oncology, vol. 25, No. 4, 1 page (2014).
Davies et al. "Antibody-Antigen Complexes", Annual Rev Biochem, vol. 59, p. 439-473 (1990).
Degaki T.L., et al. "Generation of Humanized Rebmab 200," 9th PEAC Conference on Protein Expression in Animal Cells, Jackson Hole, Wyoming, USA, Sep. 19-23, 2009, p. 1-2.
Doronina et al. "Development of potent monoclonal antibody auristatin conjugates for cancer therapy", Nature Biotechnology, vol. 21, No. 7, 778-784 (2003).
Dos Santos et al. "Rebmab200, a Humanized Monoclonal Antibody Targeting the Sodium Phosphate Transporter NaPi2b Displays Strong Immune Mediated Cytotoxicity against Cancer: A Novel Reagent for Targeted Antibody Therapy of Cancer", PLOS One, vol. 8, No. 7, e70332, p. 1-10 (2013).
Dos Santos, M. L. et al. "Generation of a Stable Cell Line for Rebmab 200 MAB," 22nd ESACT Meeting Vienna, Austria, May 15-18, 2011, p. 1-2.
Dos Santos, M. L. et al. "Flow cytometry characteristics of Rebmab 200," 9th PEAC Conference, Jackson Hole, Wyoming, USA, Sep. 19-23, 2009, p. 1-2.
Dos Santos, M. L. et al., "Stability analysis of Humanized Rebmab 100 monoclonal antibody," 9th PEAC Conference, Jackson Hole, Wyoming, USA, Sep. 19-23, 2009, p. 1-2.
Eisenhauer E.A., et al. "New response evaluation criteria in solid tumors: Revised RECIST guideline (version 1.1)," European Journal of Cancer, vol. 45, p. 228-247 (2009).
Forster, I. et al. "Phosphate transporters of the SLC20 and SLC34 families", Molecular Aspects of Medicine, 34, p. 386-395 (2013).
Gao et al. "Integrative Analysis of Complex Cancer Genomics and Clinical Profiles Using the cBioPortal", Science Signaling, vol. 6, Issue 269, p. 1-20, (2013).
Gerber, D. et al. "Safety, Pharmacokinetics, and Activity of the Anti-NaPi2b Antibody-Drug Conjugate DNIB0600A: A Phase I Study in Patients with Non-Small Cell Lung Cancer and Platinum-Resistant Ovarian Cancer", (poster), 1 page, (2013).
Gordon et al. "A phase I study of the safety and pharmacokinetics of DNIB0600A, an anti-NaPi2b antibody-drug-conjugate (ADC), in patients (pts) with non-small cell lung cancer (NSCLC) and platinum-resistant ovarian cancer (OC)", Journal of Clinical Oncology, vol. 31, No. 15, suppl., Abstract No. 2507, p. 1-4 (2013).
Grill, et al. "Hypercalcemia of Malignancy", Reviews in Endocrine & Metabolic Disorders, vol. 1, p. 253-263 (2000).
Harvey, et al. "Estrogen Receptor Status by Immunohistochemistry Is Superior to the Ligand-Binding Assay for Predicting Response to Adjuvant Endocrine Therapy in Breast Cancer", Journal of Clinical Oncology, vol. 17, No. 5, p. 1474-1474, (1999).
Ikezoe, "Pathogenesis of disseminated intravascular coagulation in patients with acute promyelocytic leukemia, and its treatment using recombinant human soluble thrombomodulin", Journal of Hematology, vol. 100, p. 27-37 (2014).
Kabat et al. "Sequences of Proteins of Immunological Interest", 5th edit. NIH Publication No. 91-3242, U.S. Dept of Health & Human Services, p. 1-4, (1991).
Kiyamova, R. et al. "Immunohistochemical Analysis of NAPI2B Protein (MX35 Antigen) Expression and Subcellular Localization in Human Normal and Cancer Tissues", Experimental Oncology, vol. 33, No. 3, p. 157-161 (2011).
Lin, K. et al. "Preclinical Development of an Anti-NaPi2b (SLC34A2) Antibody-Drug Conjugate as a Therapeutic for Non-Small Cell Lung and Ovarian Cancers", Clinical Cancer Research, vol. 21, No. 22, p. 5139-5150 (2015).
Lindegren S., et al. "Binding Affinity, Specificity and Comparative Biodistribution of the Parental Murine Monoclonal Antibody MX35 (Anti-NaPi2b) and Its Humanized Version Rebmab200", PLOS One, p. 1-16 (2015).
Malmqvist M. "Biospecific interaction analysis using biosensor technology", Nature, vol. 361, p. 186-187 (1993).
Mattes, M. et al. "Mouse Monoclonal Antibodies to Human Epithelial Differentiation Antigens Expressed on the Surface of Ovarian Carcinoma Ascites Cells", Cancer Research, 47, p. 6741-6750 (1987).
Morrison, "Success in Specification", Nature, vol. 368, p. 812-813, (1994).
Mosher R. et al., "Abstract B119: Relationship of NaPi2b expression and efficacy of XMT-1536, a NaPi2b targeting antibody-drug conjugate (ADC), in an unselected panel of human primary ovarian mouse xenograft models", AACR-NCI-EORTC International Conference: Molecular Targets and Cancer Therapeutics, vol. 17(S1), p. 1-2, (2018).
Needleman et al. "A General Method Applicable to the Search for Similarities in the Amino Acid Sequence of Two Proteins", J. Mol. Biol. vol. 48, p. 443-453 (1970).
O'Marcaigh A.S. et al. "Estimating the Predictive Value of a Diagnostic Test, How To Prevent Misleading or Confusing Results," Clinical Pediatrics vol. 32, No. 8, p. 485-491 (1993).
Pearson et al. "Improved tools for biological sequence comparison", Proc. Natl. Acad. Sci. USA, vol. 85, p. 2444-2448 (1988).
Rangel, L. et al. "Characterization of novel human ovarian cancer-specific transcripts (HOSTs) identified by serial analysis of gene expression", Oncogene, 22, p. 7225-7232 (2003).

(56) References Cited

OTHER PUBLICATIONS

Saber H., et al. "An FDA oncology analysis of antibody-drug conjugates," Regulatory Toxicology and Pharmacology, vol. 71, p. 444-452 (2015).
Shultz, "Clinical Interpretation of Laboratory Procedures," Chapter 14, in Teitz "Fundamentals of Clinical Chemistry", 4th edition, p. 192-199 (1996).
Smith et al. "Comparison of Biosequences", Advances in Applied Mathematics, vol. 2, p. 482-489 (1981).
Soares, et al. "In Silico Analysis and Immunohistochemical Characterization of NaPi2b Protein Expression in Ovarian Carcinoma with Monoclonal Antibody Mx35" Applied Immunohistochemistry and Molecular Morphology, vol. 20, No. 2, p. 165-172 (2012).
Tan et al., "A human-mouse chimeric immunoglobulin gene with a human variable region is expressed in mouse myeloma cells," The Journal of Immunology, vol. 135, No. 5, p. 3564-3567 (1985).
Thornton et al. "Prediction of progress at last" Nature, vol. 354, p. 105-106 (1991).
Wagner, C. et al. "The SLC34 family of sodium-dependent phosphate transporters", Eur J Physiol, 466, p. 139-153 (2014).
Wilkerson et al. "Prediction of Lung Cancer Histological Types by RT-qPCR Gene Expression in FFPE Specimens", The Journal of Molecular Diagnostics, vol. 15, No. 4, p. 485-497 (2013).
Wilkinson D. "Ultimate Abs", The Scientist, vol. 14, No. 8 pp. 25-28 (2000).
Xu et al. "Molecular Cloning, Functional Characterization, Tissue Distribution, and Chromosomal Localization of a Human, Small Intestinal Sodium-Phosphate (Na+-$P_i$) Transporter (SLC34A2)", Genomics, vol. 62, p. 281-284 (1999).
Yin, B. W.T. et al. "Monoclonal antibody MX35 detects the membrane transporter NaPi2b (SLC34A2) in human carcinomas", Cancer Immunity, vol. 8, 1-9, (2008).
Zweig et al., "ROC Curve Analysis: An Example Showing the Relationships Among Serum Lipid and Apolipoprotein Concentrations in Identifying Subjects with Coronary Artery Disease," Clin. Chem., vol. 38, No. 8, p. 1425-1428 (1992).

\* cited by examiner

SEQUENCE LISTING

<160> NUMBER OF SEQ ID NOS: 15

<210> SEQ ID NO 1
<211> LENGTH: 449
<212> TYPE: PRT
<213> ORGANISM: Homo sapiens

<400> SEQUENCE: 1

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Val | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Gly | Tyr |
| | | | 20 | | | | | 25 | | | | | 30 | | |
| Asn | Ile | His | Trp | Val | Lys | Gln | Ala | Pro | Gly | Gln | Gly | Leu | Glu | Trp | Ile |
| | | | 35 | | | | | 40 | | | | | 45 | | |
| Gly | Ala | Ile | Tyr | Pro | Gly | Asn | Gly | Asp | Thr | Ser | Tyr | Lys | Gln | Lys | Phe |
| | 50 | | | | | 55 | | | | | 60 | | | | |
| Arg | Gly | Arg | Ala | Thr | Leu | Thr | Ala | Asp | Thr | Ser | Thr | Ser | Thr | Val | Tyr |
| 65 | | | | | 70 | | | | | 75 | | | | | 80 |
| Met | Glu | Leu | Ser | Ser | Leu | Arg | Ser | Glu | Asp | Ser | Ala | Val | Tyr | Tyr | Cys |
| | | | | 85 | | | | | 90 | | | | | 95 | |
| Ala | Arg | Gly | Glu | Thr | Ala | Arg | Ala | Thr | Phe | Ala | Tyr | Trp | Gly | Gln | Gly |
| | | | | 100 | | | | | 105 | | | | | 110 | |
| Thr | Leu | Val | Thr | Val | Ser | Ser | Gly | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | | 180 | | | | | 185 | | | | | 190 | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | 325 | | | | | 330 | | | | | 335 | | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | | | 355 | | | | | 360 | | | | | 365 | |

```
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
                435                 440                 445
Gly

<210> SEQ ID NO 2
<211> LENGTH: 215
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Gly Asn Phe
            20                  25                  30
Leu Asn Trp Tyr Gln Gln Lys Pro Gly Lys Thr Val Lys Val Leu Ile
        35                  40                  45
Tyr Tyr Thr Ser Ser Leu Tyr Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Tyr Ser Lys Leu Pro Leu
                85                  90                  95
Thr Phe Gly Gln Gly Thr Lys Leu Glu Leu Lys Arg Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 3
<211> LENGTH: 120
<212> TYPE: PRT
<213> ORGANISM: Homo sapiens

<400> SEQUENCE: 3

Gln Val Gln Leu Val Gln Ser Gly Ala Glu Val Val Lys Pro Gly Ala
1               5                   10                  15
Ser Val Lys Met Ser Cys Lys Ala Ser Gly Tyr Thr Phe Thr Gly Tyr
```

```
                     20                  25                  30
Asn Ile His Trp Val Lys Gln Ala Pro Gly Gln Gly Leu Glu Trp Ile
             35                  40                  45
Gly Ala Ile Tyr Pro Gly Asn Gly Asp Thr Ser Tyr Lys Gln Lys Phe
         50                  55                  60
Arg Gly Arg Ala Thr Leu Thr Ala Asp Thr Ser Thr Ser Thr Val Tyr
 65                  70                  75                  80
Met Glu Leu Ser Ser Leu Arg Ser Glu Asp Ser Ala Val Tyr Tyr Cys
                 85                  90                  95
Ala Arg Gly Glu Thr Ala Arg Ala Thr Phe Ala Tyr Trp Gly Gln Gly
             100                 105                 110
Thr Leu Val Thr Val Ser Ser Gly
             115                 120
```

<210> SEQ ID NO 4
<211> LENGTH: 108
<212> TYPE: PRT
<213> ORGANISM: Homo sapiens

<400> SEQUENCE: 4

```
Asp Ile Gln Met Thr Gln Ser Pro Ser Ser Leu Ser Ala Ser Val Gly
 1               5                  10                  15
Asp Arg Val Thr Ile Thr Cys Ser Ala Ser Gln Asp Ile Gly Asn Phe
             20                  25                  30
Leu Asn Trp Tyr Gln Gln Lys Pro Gly Lys Thr Val Lys Val Leu Ile
         35                  40                  45
Tyr Tyr Thr Ser Ser Leu Tyr Ser Gly Val Pro Ser Arg Phe Ser Gly
     50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Gln Tyr Ser Lys Leu Pro Leu
                 85                  90                  95
Thr Phe Gly Gln Gly Thr Lys Leu Glu Leu Lys Arg
             100                 105
```

<210> SEQ ID NO 5
<211> LENGTH: 10
<212> TYPE: PRT
<213> ORGANISM: Homo sapiens

<400> SEQUENCE: 5

```
Gly Tyr Thr Phe Thr Gly Tyr Asn Ile His
 1               5                  10
```

<210> SEQ ID NO 6
<211> LENGTH: 17
<212> TYPE: PRT
<213> ORGANISM: Homo sapiens

<400> SEQUENCE: 6

```
Ala Ile Tyr Pro Gly Asn Gly Asp Thr Ser Tyr Lys Gln Lys Phe Arg
 1               5                  10                  15
Gly
```

<210> SEQ ID NO 7
<211> LENGTH: 10
<212> TYPE: PRT
<213> ORGANISM: Homo sapiens

```
<400> SEQUENCE: 7

Gly Glu Thr Ala Arg Ala Thr Phe Ala Tyr
1               5                   10

<210> SEQ ID NO 8
<211> LENGTH: 11
<212> TYPE: PRT
<213> ORGANISM: Homo sapiens

<400> SEQUENCE: 8

Ser Ala Ser Gln Asp Ile Gly Asn Phe Leu Asn
1               5                   10

<210> SEQ ID NO 9
<211> LENGTH: 7
<212> TYPE: PRT
<213> ORGANISM: Homo sapiens

<400> SEQUENCE: 9

Tyr Thr Ser Ser Leu Tyr Ser
1               5

<210> SEQ ID NO 10
<211> LENGTH: 9
<212> TYPE: PRT
<213> ORGANISM: Homo sapiens

<400> SEQUENCE: 10

Gln Gln Tyr Ser Lys Leu Pro Leu Thr
1               5

<210> SEQ ID NO 11
<211> LENGTH: 329
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 357
<212> TYPE: DNA
<213> ORGANISM: Homo sapiens

<400> SEQUENCE: 13
caagttcagc tggttcagtc tggcgccgag gttgtgaaac ctggcgcctc tgtgaagatg     60
agctgcaagg ccagcggcta caccttcacc ggctacaaca tccactgggt caagcaggcc    120
cctggacagg gactcgaatg gatcggagcc atctatcccg gcaacggcga caccagctac    180
aagcagaagt tccggggcag agccacactg accgccgata agcaccagac ccgtgtac     240 atggaactga gcagcctgag aagcgaggac agcgccgtgt actattgcgc cagaggcgaa    300
acagccagag ccacctttgc ctattgggcc agggaaccc tggtcaccgt tagctct       357
```

<210> SEQ ID NO 14
<211> LENGTH: 321
<212> TYPE: DNA
<213> ORGANISM: Homo sapiens

<400> SEQUENCE: 14

| | |
|---|---|
| gatattcaga tgacacagag ccccagcagc ctgtctgcct ctgtgggaga cagagtgacc | 60 |
| atcacctgta gcgccagcca ggatatcggc aacttcctga actggtatca gcagaaaccc | 120 |
| ggcaagaccg tgaaggtgct gatctactac acctccagcc tgtacagcgg cgtgcccagc | 180 |
| agatttctg gcagcggctc tggcaccgac tacaccctga ccatatctag cctgcagcct | 240 |
| gaggacttcg ccacctacta ctgccagcag tacagcaagc tgcccctgac atttggccag | 300 |
| ggcaccaagc tggaactgaa g | 321 |

<210> SEQ ID NO 15
<211> LENGTH: 690
<212> TYPE: PRT
<213> ORGANISM: Homo sapiens

<400> SEQUENCE: 15

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Gly Phe Leu Tyr Phe Phe Val
            100                 105                 110

Cys Ser Leu Asp Ile Leu Ser Ser Ala Phe Gln Leu Val Gly Gly Lys
        115                 120                 125

Met Ala Gly Gln Phe Phe Ser Asn Ser Ser Ile Met Ser Asn Pro Leu
    130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
        195                 200                 205

Glu Phe Arg Arg Ala Phe Ala Gly Ala Thr Val His Asp Phe Phe Asn
    210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

-continued

```
Lys Leu Ile Val Gln Leu Asp Lys Val Ile Ser Gln Ile Ala Met
            275                 280                 285
Asn Asp Glu Lys Ala Lys Asn Lys Ser Leu Val Lys Ile Trp Cys Lys
290                 295                 300
Thr Phe Thr Asn Lys Thr Gln Ile Asn Val Thr Val Pro Ser Thr Ala
305                 310                 315                 320
Asn Cys Thr Ser Pro Ser Leu Cys Trp Thr Asp Gly Ile Gln Asn Trp
                325                 330                 335
Thr Met Lys Asn Val Thr Tyr Lys Glu Asn Ile Ala Lys Cys Gln His
            340                 345                 350
Ile Phe Val Asn Phe His Leu Pro Asp Leu Ala Val Gly Thr Ile Leu
        355                 360                 365
Leu Ile Leu Ser Leu Leu Val Leu Cys Gly Cys Leu Ile Met Ile Val
    370                 375                 380
Lys Ile Leu Gly Ser Val Leu Lys Gly Gln Val Ala Thr Val Ile Lys
385                 390                 395                 400
Lys Thr Ile Asn Thr Asp Phe Pro Phe Pro Phe Ala Trp Leu Thr Gly
                405                 410                 415
Tyr Leu Ala Ile Leu Val Gly Ala Gly Met Thr Phe Ile Val Gln Ser
            420                 425                 430
Ser Ser Val Phe Thr Ser Ala Leu Thr Pro Leu Ile Gly Ile Gly Val
        435                 440                 445
Ile Thr Ile Glu Arg Ala Tyr Pro Leu Thr Leu Gly Ser Asn Ile Gly
    450                 455                 460
Thr Thr Thr Thr Ala Ile Leu Ala Ala Leu Ala Ser Pro Gly Asn Ala
465                 470                 475                 480
Leu Arg Ser Ser Leu Gln Ile Ala Leu Cys His Phe Phe Asn Ile
                485                 490                 495
Ser Gly Ile Leu Leu Trp Tyr Pro Ile Pro Phe Thr Arg Leu Pro Ile
            500                 505                 510
Arg Met Ala Lys Gly Leu Gly Asn Ile Ser Ala Lys Tyr Arg Trp Phe
        515                 520                 525
Ala Val Phe Tyr Leu Ile Ile Phe Phe Leu Ile Pro Leu Thr Val
    530                 535                 540
Phe Gly Leu Ser Leu Ala Gly Trp Arg Val Leu Val Gly Val Gly Val
545                 550                 555                 560
Pro Val Val Phe Ile Ile Ile Leu Val Leu Cys Leu Arg Leu Leu Gln
                565                 570                 575
Ser Arg Cys Pro Arg Val Leu Pro Lys Lys Leu Gln Asn Trp Asn Phe
            580                 585                 590
Leu Pro Leu Trp Met Arg Ser Leu Lys Pro Trp Asp Ala Val Val Ser
        595                 600                 605
Lys Phe Thr Gly Cys Phe Gln Met Arg Cys Cys Cys Cys Arg Val
    610                 615                 620
Cys Cys Arg Ala Cys Cys Leu Leu Cys Asp Cys Pro Lys Cys Cys Arg
625                 630                 635                 640
Cys Ser Lys Cys Cys Glu Asp Leu Glu Glu Ala Gln Glu Gly Gln Asp
                645                 650                 655
Val Pro Val Lys Ala Pro Glu Thr Phe Asp Asn Ile Thr Ile Ser Arg
            660                 665                 670
```

-continued

```
Glu Ala Gln Gly Glu Val Pro Ala Ser Asp Ser Lys Thr Glu Cys Thr
            675                 680                 685
Ala Leu
    690
```

NAPI2B-TARGETED POLYMER ANTIBODY-DRUG CONJUGATES AND METHODS OF USE THEREOF

RELATED APPLICATIONS

This application claims priority to, and the benefit of, U.S. provisional application Nos. 62/719,189, filed Aug. 17, 2018; 62/733,380 filed Sep. 19, 2018, 62/808,376 filed Feb. 21, 2019 and 62/854,701 filed May 30, 2019, under 35 USC § 119(e). The contents of each of these applications are hereby incorporated by reference in their entireties.

INCORPORATION BY REFERENCE OF SEQUENCE LISTING

The contents of the text file named "MRSN-026_001US_SeqList.txt", which was created on Aug. 13, 2019 and is 20 KB in size, are hereby incorporated by reference in their entirety.

FIELD OF THE INVENTION

This disclosure relates generally to dosing regimens for administering NaPi2b targeted polymer antibody-drug conjugates for the treatment of cancer.

BACKGROUND OF THE INVENTION

NaPi2b (SLC34A2, NaPiIIb, Npt2), a multi-transmembrane, sodium-dependent phosphate transporter (Xu et al. Genomics 62:281-284 (1999)), is normally expressed at the brush border membrane of mammalian small intestine and participates in the transcellular inorganic phosphate (Pi) absorption, contributing to the maintenance of phosphate homeostasis in the body. The expression of NaPi2b at the protein level has been detected in the liver, at the apical surface of epithelial cells of mammary, salivary glands, and bronchi, and in the lungs, testis, thyroid gland, small intestine, and uterus. Mutations in NaPi2b have been associated with clinical syndromes of alveolar and testicular micro lithiasis. NaPi2b is highly expressed in non-squamous non-small cell lung cancer (NSCLC), non-mucinous ovarian cancer and papillary thyroid cancer. NaPi2b-positive tissue immunoreactivity is present in 61% of NSCLC, and 92% ovarian cancer specimens.

Ovarian cancer is one of the most common gynecologic malignancies and the fifth most frequent cause of cancer death in women. The high mortality rate results in part from the frequent diagnosis of ovarian cancer at advanced stages and the mortality rate is approximately 65% of the incidence rate. Epithelial tumors of ovary comprise 58% of all ovarian neoplasms and more than 90% of malignant tumors of ovary. Debulking surgery and platinum-based combination chemotherapy (including taxanes) are current treatment modalities; however, the majority of patients with relapsed epithelial ovarian cancer eventually succumb to the disease. There is a need for novel treatment modalities in ovarian cancer, including targeted therapies such as immunotherapy with monoclonal antibodies or cancer vaccine-based approaches.

NSCLC is any type of epithelial lung cancer other than small cell lung carcinoma (SCLC). NSCLC accounts for about 85% of all lung cancers. As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy). In the metastatic or inoperative setting, chemotherapy and/or immunotherapy is used, although the disease at this stage is largely incurable and survival times remains short. There is a need for novel treatment modalities in NSCLC, including targeted therapies such as immunotherapy with monoclonal antibodies or cancer vaccine-based approaches.

Accordingly, a need exists for therapies that target the biological activities of NaPi2b.

SUMMARY OF THE INVENTION

In various aspects the invention provides methods of treating a NaPi2b expressing tumor in a subject by administering to the subject a NaPi2b-targeted fully human or humanized antibody polymer-drug conjugate. The polymer drug conjugate is administered intravenously by an infusion by at a dose of about between 10 mg/m$^2$ to 30 mg/m$^2$ on the first day of treatment and every three weeks thereafter. For example, the dose is about 11.5 mg/m$^2$ to about 12.5 mg/m$^2$, about 19.5 mg/m$^2$ to about 20.5 mg/m$^2$, about 24.5 mg/m$^2$ to about 25.5 mg/m$^2$, about 29.5 mg/m$^2$ to about 31.5 mg/m$^2$, Preferably the dose is about 12 mg/m$^2$ or about 30 mg/m$^2$.

In another aspect the invention provides methods of treating a NaPi2b expressing tumor in a subject by administering to the subject a NaPi2b-targeted fully human or humanized antibody polymer-drug conjugate intravenously by an infusion by at a dose of about between 10 mg/m$^2$ to 30 mg/m$^2$, about between 10 mg/m$^2$ to 36 mg/m$^2$ or about between 10 mg/m$^2$ to 45 mg/m$^2$ on the first day of treatment and every four weeks thereafter. For example, the dose is about 11.5 mg/m$^2$ to about 12.5 mg/m$^2$, about 19.5 mg/m$^2$ to about 20.5 mg/m$^2$, about 24.5 mg/m$^2$ to about 25.5 mg/m$^2$, about 29.5 mg/m$^2$ to about 31.5 mg/m$^2$, about 32.5 mg/m$^2$ to about 33.5 mg/m$^2$, about 35.5 mg/m$^2$ to about 36.5 mg/m$^2$, about 39.5 mg/m$^2$ to about 41.5 mg/m$^2$, about 42.5 mg/m$^2$ to about 43.5 mg/m$^2$, or about 43 mg/m$^2$ to about 45 mg/m$^2$. Preferably the dose is about 30 mg/m$^2$ or about 33 mg/m$^2$ or about 36 mg/m$^2$ or about 40 mg/m$^2$ or about 43 mg/m$^2$.

Preferably, the dose is about 10 mg/m$^2$, 15 mg/m$^2$, 20 mg/m$^2$, 25 mg/m$^2$, 30 mg/m$^2$, 33 mg/m$^2$, 36 mg/m$^2$, 40 mg/m$^2$, 43 mg/m$^2$, 43 mg/m$^2$, 44 mg/m$^2$, 45 mg/m$^2$ or the dose is about 10 mg/m$^2$, 15 mg/m$^2$, 20 mg/m$^2$, 25 mg/m$^2$, 30 mg/m$^2$, 33 mg/m$^2$, 36 mg/m$^2$, 40 mg/m$^2$ or the dose is about 10 mg/m$^2$, 15 mg/m$^2$, 20 mg/m$^2$, 25 mg/m$^2$, 30 mg/m$^2$, 33 mg/m$^2$, 36 mg/m$^2$ or the dose is about 10 mg/m$^2$, 15 mg/m$^2$, 20 mg/m$^2$, 25 mg/m$^2$ or 30 mg/m$^2$, 33 mg/m$^2$ or the dose is about 10 mg/m$^2$, 15 mg/m$^2$, 20 mg/m$^2$, 25 mg/m$^2$ or 30 mg/m$^2$, or the dose is about 10 mg m$^2$, 15 mg/m$^2$, 20 mg/m$^2$ or 25 mg/m$^2$ infused intravenously once every four weeks.

The NaPi2b antibody contains CDRH1 having the amino acid sequence GYTFTGYNIH (SEQ ID NO: 5); a CDRH2 having the amino acid sequence AIYPGNGDTSYKQKFRG (SEQ ID NO: 6); a CDRH3 having the amino acid sequence GETARATFAY (SEQ ID NO: 7); a CDRL1 having the amino acid sequence SASQDIGNFLN (SEQ ID NO: 8); a CDRL2 having the amino acid sequence YTSSLYS (SEQ ID NO: 9); and a CDRL3 having the amino acid sequence QQYSKLPLT (SEQ ID NO: 10);

The polymer-drug conjugate contains Formula A:
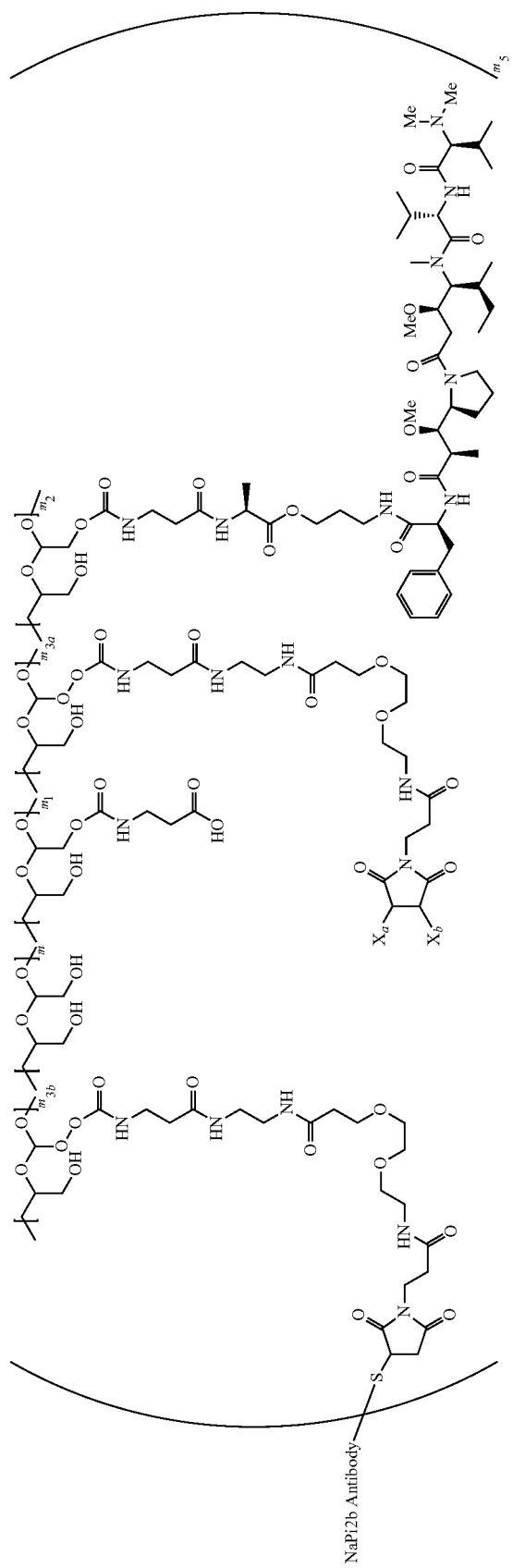

wherein:
the polymer comprises poly(1-hydroxymethylethylene hydroxymethyl-formal) (PHF) having a molecular weight ranging from about 5 kDa to about 10 kDa;
m is an integer from 20 to 75,
$m_1$ is an integer from about 5 to about 35,
$m_2$ is an integer from about 3 to about 10,
$m_{3a}$ is an integer from 0 to about 4,
$m_{3b}$ is an integer from 1 to about 5,
the sum of m, $m_1$, $m_2$, $m_{3a}$, and $m_{3b}$ ranges from about 40 to about 75, and $m_5$ is an integer from about 2 to about 5

The subject is human subject. In some aspects the subject is identified as having NaPi2b expression as detected by IHC analysis performed on a test cell population obtained from the subject. In other aspects the subject is identified as having NaPi2b expression as detected by RNA expression or a gene signature in a sample obtained from the subject.

In some aspects the NaPi2b-expressing tumor is ovarian cancer, non-small cell lung cancer (NSCLC), papillary thyroid cancer, endometrial cancer, cholangiocarcinoma, papillary renal cell cancer, clear cell renal cancer, breast cancer, kidney cancer, cervical cancer or salivary duct cancer.

In yet another aspect the subject has epithelial ovarian cancer, fallopian tube cancer, primary peritoneal cancer, platinum resistant ovarian cancer, non-squamous NSCLC cancer, progressive, radioactive iodine-refractory, loco-regional recurrent or metastatic disease papillary thyroid cancer or epithelial endometrial cancer.

In yet another aspect the subject having epithelial ovarian cancer is subtyped as high-grade ovarian cancer, low-grade serous ovarian cancer or clear cell ovarian cancer.

In yet another aspect the subject having ovarian cancer has received prior single agent chemotherapy such as, for example, pegylated liposomal doxorubicin, weekly treatment with paclitaxel topotecan gemcitabine, PARP inhibitor and the like.

In yet another aspect the subject having ovarian cancer has received no more than 3 lines of prior lines of therapy such as, for example, including but not limited to, chemotherapy combination, such as, for example, carboplatin plus paclitaxel, pegylated liposomal doxorubicin, weekly treatment with paclitaxel, docetaxel, topotecan, gemcitabine, PARP inhibitor and the like. In a further aspect the subject having NSCLC cancer is subtyped as adenocarcinoma.

In another aspect the subject has NSCLC and has received prior treatment, such as for example, with a platinum-based chemotherapy (cisplatin or carboplatin) and a PD-1 or PD-L1 monoclonal antibody. In another aspect the subject has NSCLC and has received prior treatment with carboplatin/paclitaxel, abraxane nab-paclitaxel, docetaxel, premetrexed, gemcitabine or a combination of docetaxel and ramucirumab.

In another aspect the subject has NSCLC and has not received additional prior treatment with a cytotoxic agent or has not received immunotherapy. In another aspect the subject having NSCLC has documented intolerance or disease progression with known oncogenic mutations for which there are approved therapies (e.g. ALK translocation, EGFR mutation).

In a further aspect the subject having NSCLC cancer is treated with a polymer-drug conjugate of Formula A and a PD-1 or PD-L1 monoclonal antibody, such as, for example, nivolumab, pembrolizumab, atezolizumab or avelumab In another aspect the subject has papillary thyroid cancer with resistance or intolerance to prior kinase inhibitor therapy or has received prior treatment for low-grade, hormone receptor-positive endometroid adenocarcinoma.

In another aspect the endometrial cancer is not a stromal tumor or a carcinosarcoma.

In another aspect the subject has endometrial cancer and has received prior treatment with a carboplatin/paclitaxel or a similar regimen.

In another aspect the subject has papillary renal cell cancer or clear cell renal cancer that has a predominantly papillary growth pattern. In one aspect the subject has a histologic diagnosis of salivary duct cancer has progressed after standard systemic therapy.

In yet another aspect, the subject is refractory to chemotherapy, including standard, front-line chemotherapeutic agents.

In a further aspect the subject is treated with a polymer-drug conjugate of Formula A in combination with a PARP inhibitor, such as, for example, olaparib, niraparib, rucaparib, talazoparib, and the like; a PD1/PDL-1 inhibitor, such as, for example, nivolumab, pembrolizumab, atezolizumab, avelumab, and the like; chemotherapy, such as, for example, carboplatin, cisplatin, oxaliplatin, doxil, cyclophosphamide, gemcitabine, topotecan, premetrexe, and the like; a VEGF inhibitor, such as, for example, bevacizumab, ramucirumab, and the like; a tyrosine kinase inhibitor, such as, for example, gefitinib, afatinib, erlotinib, dacomitinib, osimertinib, pazopanib, and the like; an ALK inhibitor, such as, for example, alectinib, crizotinib, certinib, brigatinib, and the like; or a BRAF inhibitor, such as, for example, dabrafenib, trametinib, and the like.

In another aspect, the subject is treated with a polymer-drug conjugate of Formula A in combination with pembrolizumab, carboplatin, doxil, bevacizumab or a PARP inhibitor.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Figure 1:
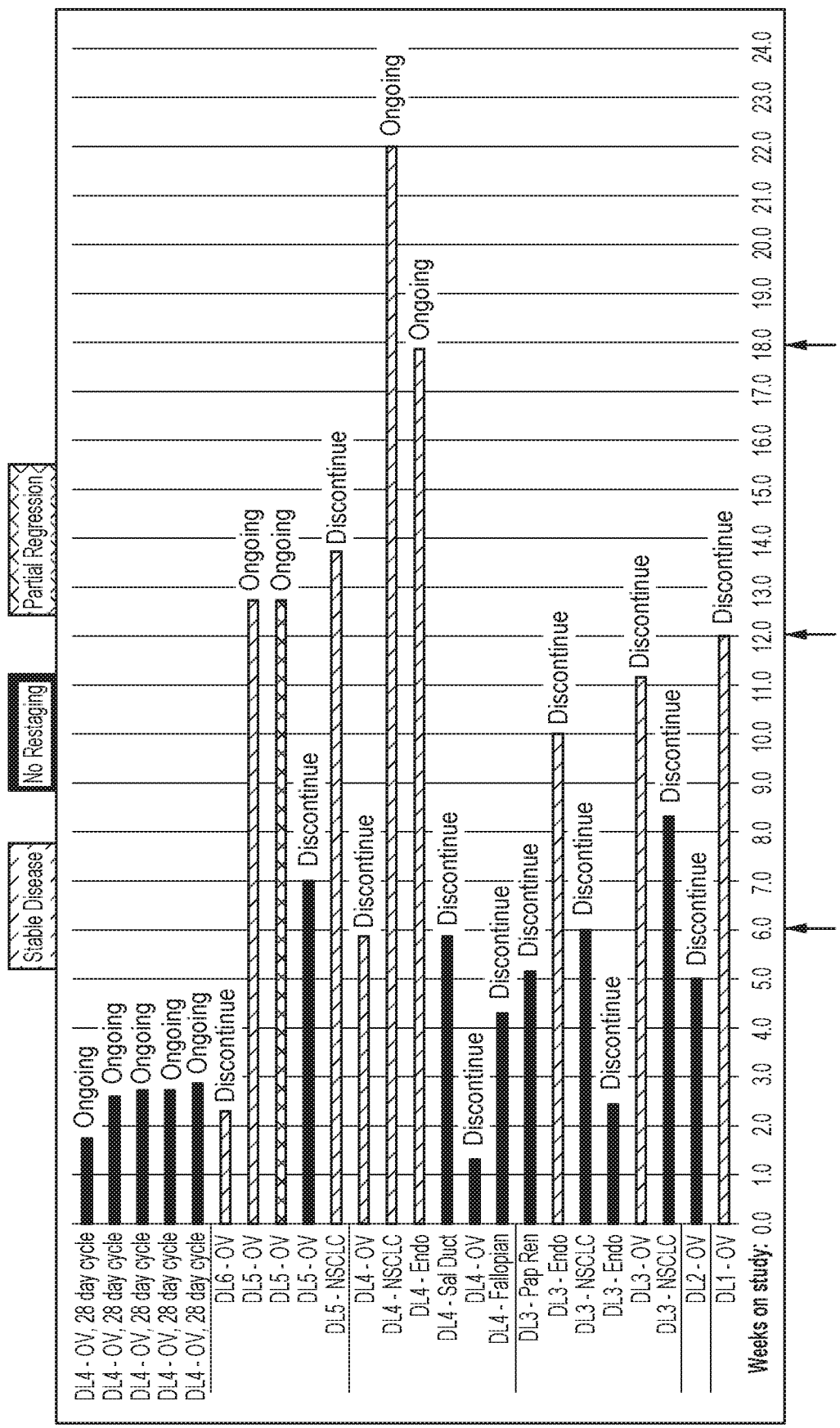
FIG. 1 is a swimmers plot that summarizes details for the time on study for all patients though DL6, 21 day cycle, (n=19) and four patient dosed patients in the 28-day cycle (n=4).

The present disclosure provides methods of treating NaPi2b expressing cancer by administering a NaPi2b-targeted polymer antibody-drug conjugate that specifically bind to the extracellular region of SLC34A2. Specifically, the invention provides dosing regimens for XMT-1536 in the treatment of NaPi2b expressing cancers. XMT-1536 is comprised of about 10-15 molecules of auristatin F-hydroxypropyl amide (AF HPA) conjugated to a cysteine moiety of a NaPi2b monoclonal antibody (XMT-1535) via a poly(1-hydroxymethylethylene hydroxymethyl-formal) (PHF) scaffold.

Patients with NaPi2b-expressing ovarian cancer, NSCLC, papillary thyroid cancer, endometrial cancer, papillary renal cell cancer or salivary duct cancer were intravenously administered XMT-1536 every three weeks in a dose escalation study. The disease control rates was 67% for patients treated with at least 12 mg/m$^2$ XMT-1536 as per RECIST, version 1.1. XMT-1536 has been well tolerated at the maximum doses administered (40 mg/m$^2$). Accordingly, the invention features methods of treating NaPi2b expressing tumors by administering to a subject, i.e., human, an infusion dose of about between 10 to 45 mg/m$^2$. Tumors include ovarian cancer, non-small cell lung cancer (NSCLC), papillary thyroid cancer, endometrial cancer, cholangiocarcinoma, papillary renal cell cancer, clear cell renal cancer, breast cancer, kidney cancer, cervical cancer or salivary duct cancer. The tumor is a primary tumor or a metastatic tumor.

Patients with NaPi2b-expressing ovarian cancer, NSCLC, papillary thyroid cancer, endometrial cancer, papillary renal cell cancer or salivary duct cancer were intravenously administered XMT-1536 every four weeks in a dose escalation study with an infusion dose of about between 20 to 45 mg/m$^2$ i.e. 20 mg/m$^2$, 25 mg/m$^2$, 30 mg/m$^2$, 33 mg/m$^2$, 36 mg/m$^2$, 40 mg/m$^2$, 43 mg/m$^2$, 44 mg/m$^2$, or 45 mg/m$^2$. The subject may or may not have received previous treatment for the cancer. For example, the subject has received platinum-based chemotherapy, PD-1 or PD-L1 regimens, or paclitaxel.

In some aspects the subject has been identified as having NaPi2b expression. NaPi2b expression is detected by methods known in the art. For example, by immunohistochemistry (IHC) analysis, fluorescent in situ hybridization (FISH) assay or RNA expression analysis.

NaPi2b Antibodies

The NaPi2b antibodies suitable for the methods of the disclosure specifically bind specific binding to the extracellular region of SLC34A2. The disclosure further provides NaPi2b-targeted monoclonal antibodies that specifically recognizes NaPi2b, also known as sodium-dependent phosphate transport protein 2B. The NaPi2b antibodies used in the conjugates disclosed herein are capable of and useful in modulating, e.g., blocking, inhibiting, reducing, antagonizing, neutralizing or otherwise interfering with at least one biological activity of NaPi2b. Antibodies disclosed herein also include antibodies that bind soluble NaPi2b. The NaPi2b antibodies specifically bind to an epitope on an extracellular domain (ECD) of the human NaPi2b. These antibodies are collectively referred to herein as "NaPi2b" antibodies.

The NaPi2b antibody-drug conjugates provided herein include antibodies that bind to a NaPi2b epitope with an equilibrium dissociation constant ($K_d$ or $K_D$) of ≤1 μM, e.g., ≤100 nM, preferably ≤10 nM, and more preferably ≤1 nM. For example, the NaPi2b antibodies used in the antibody-drug conjugates disclosed herein exhibit a $K_d$ in the range approximately between ≤1 nM to about 1 pM.

The NaPi2b antibody-drug conjugates provided herein can include antibodies that serve to modulate, block, inhibit, reduce, antagonize, neutralize or otherwise interfere with the functional activity of NaPi2b. Functional activities of NaPi2b include for example, participating in the transcellular inorganic phosphate (Pi) absorption, thereby contributing to the maintenance of phosphate homeostasis in the body. For example, the NaPi2b antibodies completely or partially inhibit NaPi2b functional activity by partially or completely modulating, blocking, inhibiting, reducing antagonizing, neutralizing, or otherwise interfering with transcellular inorganic phosphate absorption. Transcellular inorganic phosphate absorption activity is assessed using any art-recognized method for detecting transcellular inorganic phosphate absorption activity, including, but not limited to detecting levels of transcellular inorganic phosphate absorption in the presence and absence of an anti-NaPi2b antibody disclosed herein.

The NaPi2b antibodies are considered to completely modulate, block, inhibit, reduce, antagonize, neutralize or otherwise interfere with NaPi2b functional activity when the level of NaPi2b functional activity in the presence of the NaPi2b antibody is decreased by at least 95%, e.g., by 96%, 97%, 98%, 99% or 100% as compared to the level of NaPi2b functional activity in the absence of binding with a NaPi2b antibody described herein. The NaPi2b antibodies are considered to partially modulate, block, inhibit, reduce, antagonize, neutralize or otherwise interfere with NaPi2b functional activity when the level of NaPi2b activity in the presence of the NaPi2b antibody is decreased by less than 95%, e.g., 10%, 20%, 25%, 30%, 40%, 50%, 60%, 75%, 80%, 85% or 90% as compared to the level of NaPi2b activity in the absence of binding with a NaPi2b antibody described herein.

Exemplary antibodies disclosed herein include, the XMT-1535 antibody. These antibodies show specificity for human NaPi2b and they have been shown to inhibit NaPi2b activity.

NaPi2b human or humanized monoclonal antibody, XMT-1535, includes a heavy chain (HC), heavy chain variable region (VH), light chain (LC), and a light chain variable region (VL), as shown in the amino acid and corresponding nucleic acid sequences presented below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDRs) for the XMT-1535 antibody are as defined by E. A. Kabat et al. (See Kabat, E. A., et al., Sequences of Protein of immunological interest, Fifth Edition, US Department of Health and Human Services, US Government Printing Office (1991)) and are disclosed in U.S. Pat. No. 8,603,474.

>XMT-1535 Heavy Chain Amino Acid Sequence (Heavy chain variable region (SEQ ID NO: 3) (Italicized)+IgG1 Heavy chain constant region (SEQ ID NO: 11))

(SEQ ID NO: 1)
*QVQLVQSGAEVVKPGASVKMSCKASGYTFTGYNIHWVKQAP*
*GQGLEWIGAIYPGNGDTSYKQKFRGRATLTADTSTSTVYMELSSLR*
*SEDSAVYYCARGETARATFAYWGQGTLVTVSSG*ASTKGPSVFPLA
PSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPG*

(SEQ ID NO: 5)
CDRH1: GYTFTGYNIH (SEQ ID NO: 6)
CDRH2: AIYPGNGDTSYKQKFRG (SEQ ID NO: 7)
CDRH3: GETARATFAY

>XMT-1535 Heavy chain variable region nucleic acid sequence (SEQ ID NO: 13)
CAAGTTCAGCTGGTTCAGTCTGGCGCCGAGGTTGTGAAACCTGGCGCCTC
TGTGAAGATGAGCTGCAAGGCCAGCGGCTACACCTTCACCGGCTACAACA
TCCACTGGGTCAAGCAGGCCCCTGGACAGGGACTCGAATGGATCGGAGCC
ATCTATCCCGGCAACGGCGACACCAGCTACAAGCAGAAGTTCCGGGGCAG
AGCCACACTGACCGCCGATACAAGCACCAGCACCGTGTACATGGAACTGA
GCAGCCTGAGAAGCGAGGACAGCGCCGTGTACTATTGCGCCAGAGGCGAA
ACAGCCAGAGCCACCTTTGCCTATTGGGGCCAGGGAACCCTGGTCACCGT
TAGCTCT >XMT-1535 Light Chain Amino Acid Sequence (Light chain variable region (SEQ ID NO: 4) (Italicized)+Light chain constant region (SEQ ID NO: 12))

*DIQMTQSPSSLSASVGDRVTITCSASQDIGNFLNWYQ*
*QKPGKTVKVLIYYTSSLYSGVPSRFSGSGSGTDYTLTISSLQPEDFAT*
*YYCQQYSKLPLTFGQGTKLELKR*RTVAAPSVFIFPPSDEQLKSGTAS
VVCLLNNFYPREAKVQWKVDNALQSGNSQESVTEQDSKDSTYSLSSTLTL
SKADYEKHKVYACEVT (SEQ ID NO: 2)
HQGLSSPVTKSFNRGEC (SEQ ID NO: 8)
CDRL1: SASQDIGNFLN (SEQ ID NO: 9)
CDRL2: YTSSLYS (SEQ ID NO: 10)
CDRL3: QQYSKLPLT

>XMT-1535 Light chain variable region nucleic acid sequence (SEQ ID NO: 14)
GATATTCAGATGACACAGAGCCCCAGCAGCCTGTCTGCCTCTGTGGGAGA
CAGAGTGACCATCACCTGTAGCGCCAGCCAGGATATCGGCAACTTCCTGA
ACTGGTATCAGCAGAAACCCGGCAAGACCGTGAAGGTGCTGATCTACTAC
ACCTCCAGCCTGTACAGCGGCGTGCCCAGCAGATTTTCTGGCAGCGGCTC
TGGCACCGACTACACCCTGACCATATCTAGCCTGCAGCCTGAGGACTTCG
CCACCTACTACTGCCAGCAGTACAGCAAGCTGCCCCTGACATTTGGCCAG
GGCACCAAGCTGGAACTGAAG Also included in the disclosure are antibodies that bind to the same epitope or cross compete for binding to the same epitope as the antibodies described herein. For example, antibodies disclosed herein specifically bind to NaPi2b, wherein the antibody binds to an epitope that includes one or more amino acid residues on human NaPi2b (e.g., GenBank Accession No. 095436.3).

Antibodies disclosed herein specifically bind to an epitope on the full-length human NaPi2b comprising the amino acid sequence:

(SEQ ID NO: 15)
```
  1 MAPWPELGDA QPNPDKYLEG AAGQQPTAPD KSKETNKTDN TEAPVTKIEL
 51 LPSYSTATLI DEPTEVDDPW NLPTLQDSGI KWSERDTKGK ILCFFQGIGR
101 LILLLGFLYF FVCSLDILSS AFQLVGGKMA GQFFSNSSIM SNPLLGLVIG
151 VLVTVLVQSS STSTSIVVSM VSSSLLTVRA AIPIIMGANI GTSITNTIVA
201 LMQVGDRSEF RRAFAGATVH DFFNWLSVLV LLPVEVATHY LEIITQLIVE
251 SFHFKNGEDA PDLLKVITKP FTKLIVQLDK KVISQIAMND EKAKNKSLVK
301 IWCKTFTNKT QINVTVPSTA NCTSPSLCWT DGIQNWTMKN VTYKENIAKC
351 QHIFVNFHLP DLAVGTILLI LSLLVLCGCL IMIVKILGSV LKGQVATVIK
401 KTINTDFPFP FAWLTGYLAI LVGAGMTFIV QSSSVFTSAL TPLIGIGVIT
451 IERAYPLTLG SNIGTTTTAI LAALASPGNA LRSSLQIALC HFFFNISGIL
```

```
501 LWYPIPFTRL PIRMAKGLGN ISAKYRWFAV FYLIIFFFLI PLTVFGLSLA

551 GWRVLVGVGV PVVFIIILVL CLRLLQSRCP RVLPKKLQNW NFLPLWMRSL

601 KPWDAVVSKF TGCFQMRCCC CCRVCCRACC LLCDCPKCCR CSKCCEDLEE

651 AQEGQDVPVK APETFDNITI SREAQGEVPA SDSKTECTAL
```

Antibodies disclosed herein specifically bind to an epitope on an extracellular domain (ECD) of the human NaPi2b.

Those skilled in the art will recognize that it is possible to determine, without undue experimentation, if a monoclonal antibody has the same specificity as a monoclonal antibody disclosed herein (e.g., XMT-1535, 10H1.11.4B) by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. If the monoclonal antibody being tested is inhibited then, in all likelihood, it has the same, or functionally equivalent, epitopic specificity as the monoclonal antibody disclosed herein.

Screening of monoclonal antibodies disclosed herein, can also be carried out, e.g., by measuring NaPi2b-mediated activity, and determining whether the test monoclonal antibody is able to modulate, block, inhibit, reduce, antagonize, neutralize or otherwise interfere with NaPi2b activity.

The antibodies disclosed herein contain a heavy chain variable region having an amino acid sequence at least 90%, 91%, 92%, 93%, 94%, 95%, 96%, 97% 98%, 99% or more identical to a sequence selected from the group consisting of SEQ ID NOs: 3 and a light chain variable region having an amino acid sequence at least 90%, 91%, 92%, 93%, 94%, 95%, 96%, 97% 98%, 99% or more identical to a sequence selected from the group consisting of SEQ ID NOs: 4.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 1 and a light chain amino acid sequence at least 90%, 91%, 92%, 93%, 94%, 95%, 96%, 97% 98%, 99% or more identical to the amino acid sequence of SEQ ID NO: 2.

The antibodies disclosed herein contain a heavy chain variable region having an amino acid sequence at least 85%, 86%, 87% 88%, 89%, 90%, 91%, 92%, 93%, 94%, 95%, 96%, 97% 98%, 99% or more identical to a sequence selected from the group consisting of SEQ ID NOs: 3 and a light chain variable region having an amino acid sequence at least 85%, 86%, 87% 88%, 89%, 90%, 91%, 92%, 93%, 94%, 95%, 96%, 97% 98%, 99% or more identical to a sequence selected from the group consisting of SEQ ID NOs: 4.

In some embodiments, the antibodies disclosed herein contain a heavy chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 1 and a light chain amino acid sequence at least 85%, 86%, 87% 88%, 89%, 90%, 91%, 92%, 93%, 94%, 95%, 96%, 97% 98%, 99% or more identical to the amino acid sequence of SEQ ID NO: 2.

In some embodiments, the antibodies disclosed herein contain the heavy chain variable region amino acid sequence of SEQ ID NO: 3 and the light chain variable region amino acid sequence of SEQ ID NO: 4.

In some embodiments, the antibodies disclosed herein contain the heavy chain amino acid sequence of SEQ ID NO: 1 and the light chain amino acid sequence of SEQ ID NO: 2.

In some embodiments, the antibodies disclosed herein contain the CDRH1 amino acid sequence of SEQ ID NO: 5, the CDRH2 amino acid sequence of SEQ ID NO: 6, the CDRH3 amino acid sequence of SEQ ID NO: 7, the CDRL1 amino acid sequence of SEQ ID NO: 8, the CDRL2 amino acid sequence of SEQ ID NO: 9, and the CDRL3 amino acid sequence of SEQ ID NO: 10.

In some embodiments, the antibodies disclosed herein that contains the amino acid sequence at least 90%, 91%, 92%, 93%, 94%, 95%, 96%, 97% 98%, 99% or more identical to the amino acid sequence GYTFTGYNIH (SEQ ID NO: 5); a CDRH2 that contains the amino acid sequence at least 90%, 91%, 92%, 93%, 94%, 95%, 96%, 97% 98%, 99% or more identical to the amino acid sequence AIYPGNGDTSYKQKFRG (SEQ ID NO: 6); a CDRH3 that contains the amino acid sequence at least 90%, 91%, 92%, 93%, 94%, 95%, 96%, 97% 98%, 99% or more identical to the amino acid sequence GETARATFAY (SEQ ID NO: 7); a CDRL1 that contains the amino acid sequence at least 90%, 91%, 92%, 93%, 94%, 95%, 96%, 97% 98%, 99% or more identical to the amino acid sequence SASQDIGNFLN (SEQ ID NO: 8); a CDRL2 that contains the amino acid sequence at least 90%, 91%, 92%, 93%, 94%, 95%, 96%, 97% 98%, 99% or more identical to the amino acid sequence YTSSLYS (SEQ ID NO: 9); and a CDRL3 that contains the amino acid sequence at least 90%, 91%, 92%, 93%, 94%, 95%, 96%, 97% 98%, 99% or more identical to the amino acid sequence QQYSKLPLT (SEQ ID NO: 10).

In some embodiments, the antibodies disclosed herein that contains the amino acid sequence at least 85%, 86%, 87% 88%, 89%, 90%, 91%, 92%, 93%, 94%, 95%, 96%, 97% 98%, 99% or more identical to the amino acid sequence GYTFTGYNIH (SEQ ID NO: 5); a CDRH2 that contains the amino acid sequence at least 85%, 86%, 87% 88%, 89%, 90%, 91%, 92%, 93%, 94%, 95%, 96%, 97% 98%, 99% or more identical to the amino acid sequence AIYPGNGDTSYKQKFRG (SEQ ID NO: 6); a CDRH3 that contains the amino acid sequence at least 85%, 86%, 87% 88%, 89%, 90%, 91%, 92%, 93%, 94%, 95%, 96%, 97% 98%, 99% or more identical to the amino acid sequence GETARATFAY (SEQ ID NO: 7); a CDRL1 that contains the amino acid sequence at 85%, 86%, 87% 88%, 89%, 90%, 91%, 92%, 93%, 94%, 95%, 96%, 97% 98%, 99% or more identical to the amino acid sequence SASQDIGNFLN (SEQ ID NO: 8); a CDRL2 that contains the amino acid sequence at least 85%, 86%, 87% 88%, 89%, 90%, 91%, 92%, 93%, 94%, 95%, 96%, 97% 98%, 99% or more identical to the amino acid sequence YTSSLYS (SEQ ID NO: 9); and a CDRL3 that contains the amino acid sequence at least 85%, 86%, 87% 88%, 89%, 90%, 91%, 92%, 93%, 94%, 95%, 96%, 97% 98%, 99% or more identical to the amino acid sequence QQYSKLPLT (SEQ ID NO: 10).

In certain embodiments, the antibodies disclosed herein include one or more conservative amino acid substitutions in a variable domain sequence such as 1, 2, 3, 4, 5, 6, 7, 8, 9, 10, 11, 12, 13, 14, 15, or more conservative substitutions in a variable domain sequence. In some embodiments, these conservative amino acid substitutions are in a CDR region, e.g., 1, 2, 3, 4, 5, 6, 7, 8, 9, 10, 11, 12, 13, 14, 15, or more conservative substitutions are made cumulatively across all CDRs and in some particular embodiments, up to 1, 2, 3, or 4 conservative amino acid substitutions may be present in each CDR sequence, e.g., SEQ ID NOs: 5-10.

Those skilled in the art will recognize that it is possible to determine, without undue experimentation, if a monoclonal antibody has the same specificity as a monoclonal antibody XMT-1535, by ascertaining whether the former prevents the latter from binding to a natural binding partner or other molecule known to be associated with NaPi2b. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble NaPi2b (with which it is normally reactive), and then add the monoclonal antibody being tested to determine if the monoclonal antibody being tested is inhibited in its ability to bind NaPi2b. If the monoclonal antibody being tested is inhibited then, in all likelihood, it has the same, or functionally equivalent, epitopic specificity as the monoclonal antibody disclosed herein.

Screening of monoclonal antibodies disclosed herein, can be also carried out, e.g., by measuring NaPi2b-mediated activity, and determining whether the test monoclonal antibody is able to modulate, block, inhibit, reduce, antagonize, neutralize or otherwise interfere with NaPi2b activity.

The NaPi2b antibodies suitable for use in the methods disclosed herein can be generated and purified by well-known techniques e.g., WO 2009/097128, WO 2017/160754, and U.S. Ser. No. 16/136,706, each of which is incorporated herein in its entirety by reference.

NaPi2b Targeted Polymer Antibody Drug Conjugates

The invention pertains to therapies involving immunoconjugates comprising an antibody conjugated to a cytotoxic agent such as a toxin (e.g., an enzymatically active toxin of bacterial, fungal, plant, or animal origin, or fragments thereof), via a polymer scaffold.

The conjugate described herein includes a NaPi2b antibody connected to one or more AF-HPA-carrying polymeric scaffolds independently comprising poly(1-hydroxymethylethylene hydroxymethyl-formal) (PHF) having a molecular weight ranging from about 5 kDa to about 10 kDa. The AF-HPA-carrying polymeric scaffold is conjugated to the NaPi2b targeted antibody via the NaPi2b cysteine residues.

Specifically, the NaPi2b targeted polymer antibody-drug conjugate is XMT-1536 and has the Formula (A):

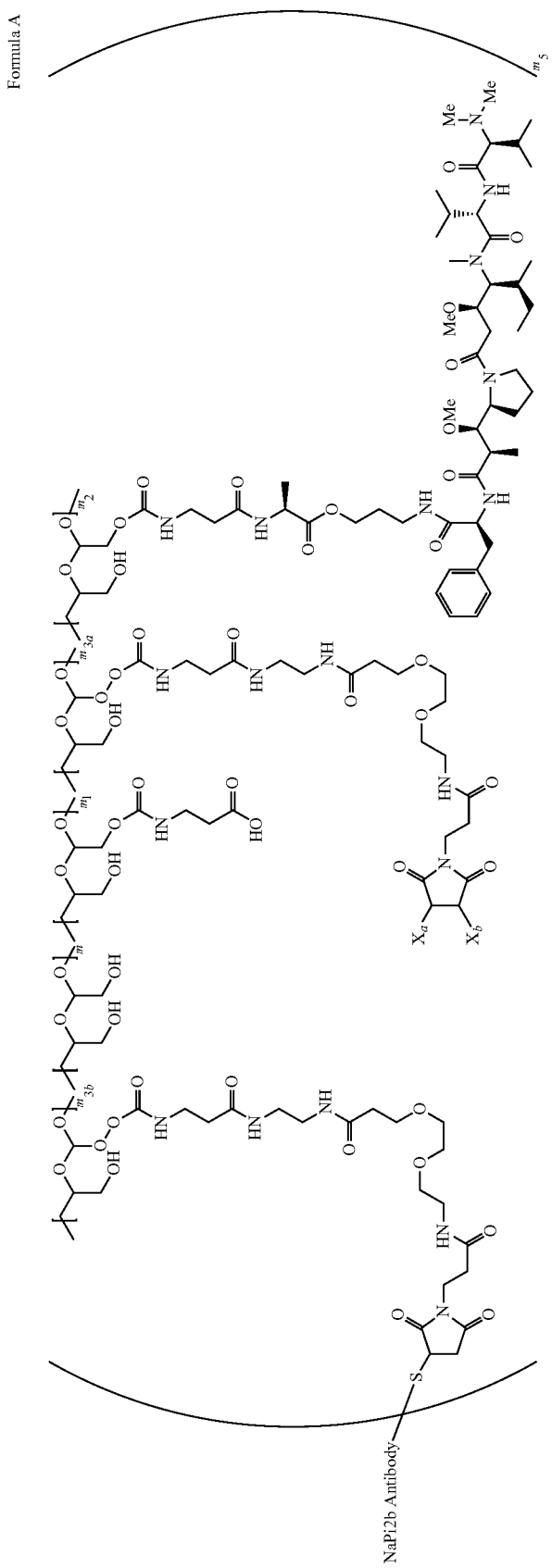

wherein:

the polymer comprises poly(1-hydroxymethylethylene hydroxymethyl-formal) (PHF) having a molecular weight ranging from about 5 kDa to about 10 kDa;

m is an integer from 20 to 75, $m_1$ is an integer from about 5 to about 35, $m_2$ is an integer from about 3 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, $m_5$ is an integer from about 2 to about 5, and NaPi2b is the fully human or humanized NaPi2b antibody XMT1535 described herein.

In some embodiments, m is an integer from about 30 to about 75.

In some embodiments, m is an integer from about 30 to about 40.

In some embodiments, $m_1$ is an integer from about 10 to about 20.

In some embodiments, $m_1$ is an integer from about 10 to about 12.

In some embodiments, $m_2$ is an integer from about 3 to about 5.

In some embodiments, $m_{3a}$ is an integer from 0 to about 1.

In some embodiments, $m_{3b}$ is an integer from 2 to about 4

In some embodiments, $m_5$ is an integer from about 2 to about 4.

In some embodiments, $m_5$ is an integer from about 3 to about 4.

In some embodiments the NaPi2b targeted polymer antibody-drug conjugate comprises 10-15 molecules of AF-HPA.

In some embodiments, the PHF has a molecular weight ranging from about 6 kDa to about 8 kDa.

In some embodiments, the PHF has a molecular weight ranging from about 6 kDa to about 7 kDa.

In certain embodiments, the NaPi2b targeted polymer antibody-drug conjugate Formula (A) is of Formula (B), wherein the polymer is PHF that has a molecular weight ranging from about 5 kDa to about 10 kDa:

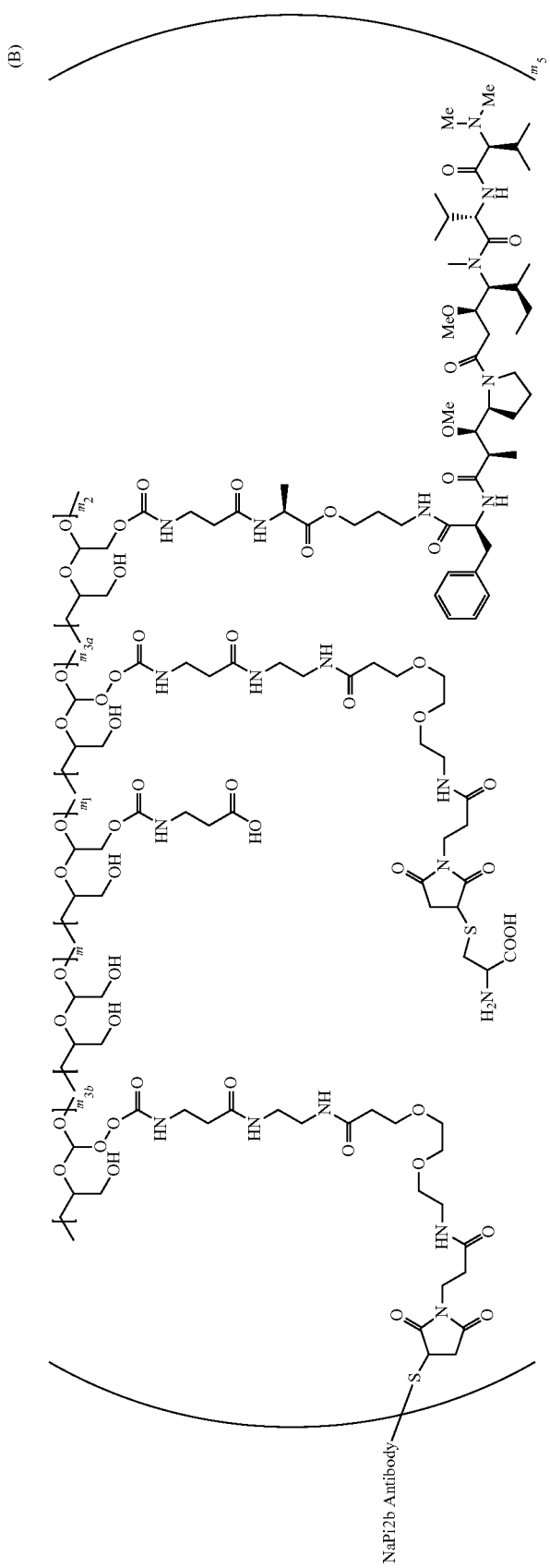

wherein:
m is an integer from 30 to about 35,
$m_1$ is an integer from 8 to about 10,
$m_2$ is an integer from 2 to about 5,
$m_{3a}$ is an integer from 0 to about 1,
$m_{3b}$ is an integer from 1 to about 2,
the sum of $m_{3a}$ and $m_{3b}$ ranges from 1 and about 4, and
the ratio between the PHF and the antibody is about 3 to about 5.

The NaPi2b targeted polymer antibody-drug conjugates, (i.e., XMT-1536) suitable for use in the methods disclosed herein can be generated and purified by well-known techniques e.g., WO 2009/097128, WO 2017/160754, PCT/US18/38988 and U.S. Ser. No. 16/136,706, each of which is incorporated herein in its entirety by reference.

Dosage and Administration

The cancer therapy provided herein, containing a NaPi2b-targeted polymer antibody-drug conjugate, is administered in an amount sufficient to exert a therapeutically useful effect. Typically, the active agents are administered in an amount that does not result in undesirable side effects of the patient being treated, or that minimizes or reduces the observed side effects. NaPi2b expressing cancers include for example, of ovarian cancer, non-small cell lung cancer (NSCLC), papillary thyroid cancer, endometrial cancer, cholangiocarcinoma, papillary renal cell cancer, clear cell renal cancer, breast cancer, kidney cancer, cervical cancer and salivary duct cancer.

It is within the level of one of skill in the art to determine the precise amounts of active agents, including NaPi2b-targeted polymer antibody-drug conjugates to be administered to a subject. For example, such agents and uses for treating cancers and solid tumors, are well-known in the art. Thus, dosages of such agents can be chosen based on standard dosing regimens for that agent under a given route of administration.

It is understood that the precise dosage and duration of treatment is a function of the tissue or tumor being treated and may be determined empirically using known testing protocols or by extrapolation from in vivo or in vitro test data and/or can be determined from known dosing regimens of the particular agent. It is to be noted that concentrations and dosage values may also vary with the age of the individual treated, the weight of the individual, the route of administration and/or the extent or severity of the disease and other factors that are within the level of a skilled medical practitioner to consider. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects). It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof.

For example, the NaPi2b-targeted polymer antibody-drug conjugate, is administered in a therapeutically effective amount to decrease the tumor volume.

The amount of a NaPi2b-targeted polymer antibody-drug conjugate is administered for the treatment of a disease or condition, for example a cancer or solid tumor can be determined by standard clinical techniques. In addition, in vitro assays and animal models can be employed to help identify optimal dosage ranges. The precise dosage, which can be determined empirically, can depend on the route of administration, the type of disease to be treated and the seriousness of the disease.

The conjugates provided herein are administered intravenously. For intravenous administration, the conjugate can be administered by push or bolus, by infusion, or via a combination thereof. The infusion time can be about 1 minute to three hours, such as about 1 minute to about two hours, or about 1 minute to about 60 minutes, or at least 10 minutes, 40 minutes, or 60 minutes.

The dosage amount is between about 10 mg/m$^2$ to 30 mg/m$^2$. For example, the dosage is between about 11.5 mg/m$^2$ to about 12.5 mg/m$^2$. Alternatively, the dosage is between about 19.5 mg/m$^2$ to about 20.5 mg/m$^2$, between about 24.5 mg/m$^2$ to about 25.5 mg/m$^2$, between about 29.5 mg/m$^2$ to about 31.5 mg/m$^2$. In some embodiments, the dosage is about 12 mg/m$^2$ about 20 mg/m$^2$, about 25 mg/m$^2$ or about 30 mg/m$^2$. In other embodiments the dosage is 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, or 30 mg/m$^2$. In these embodiments the dosage amounts are administered intravenously once every four weeks i.e. 28-day cycle.

Alternatively, the dosage amount is between about 10 mg/m$^2$ to 33 mg/m$^2$. For example, the dosage is between about 11.5 mg/m$^2$ to about 12.5 mg/m$^2$. Alternatively, the dosage is between about 19.5 mg/m$^2$ to about 20.5 mg/m$^2$, between about 24.5 mg/m$^2$ to about 25.5 mg/m$^2$, between about 29.5 mg/m$^2$ to about 31.5 mg/m$^2$, or between about 32.5 mg/m$^2$ to about 33.5 mg/m$^2$. In some embodiments, the dosage is about 12 mg/m$^2$, about 20 mg/m$^2$, about 25 mg/m$^2$, about 30 mg/m$^2$ or about 33 mg/m$^2$. In other embodiments the dosage is 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, or 33 mg/m$^2$. In these embodiments the dosage amounts are administered intravenously once every four weeks i.e. 28-day cycle.

Alternatively, the dosage amount is between about 10 mg/m$^2$ to 36 mg/m$^2$. For example, the dosage is between about 11.5 mg/m$^2$ to about 12.5 mg/m$^2$. Alternatively, the dosage is between about 19.5 mg/m$^2$ to about 20.5 mg/m$^2$, between about 24.5 mg/m$^2$ to about 25.5 mg/m$^2$, between about 29.5 mg/m$^2$ to about 31.5 mg/m$^2$, between about 32.5 mg/m$^2$ to about 33.5 mg/m$_2$, or between about 35.5 mg/m$^2$ to about 36.5 mg/m$^2$. In some embodiments, the dosage is about 12 mg/m$^2$, about 20 mg/m$^2$, about 25 mg/m$^2$, about 30 mg/m$^2$, about 33 mg/m$^2$ or about 36 mg/m$^2$. In other embodiments the dosage is 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, or 36 mg/m$^2$. In these embodiments the dosage amounts are administered intravenously once every four weeks i.e. 28-day cycle.

Alternatively the dosage amount is between about 10 mg/m$^2$ to 40 mg/m$^2$. For example, the dosage is between about 11.5 mg/m$^2$ to about 12.5 mg/m$^2$. Alternatively the dosage is between about 19.5 mg/m$^2$ to about 20.5 mg/m$^2$, between about 24.5 mg/m² to about 25.5 mg/m², between about 29.5 mg/m² to about 31.5 mg/m², between about 32.5 mg/m² to about 33.5 mg/m², between about 35.5 mg/m² to about 36.5 mg/m², between about 39.5 mg/m² to about 41.5 mg/m². In some embodiments, the dosage is about 12 mg/m², about 20 mg/m², about 25 mg/m², about 30 mg/m², about 33 mg/m², about 36 mg/m² or about 40 mg/m². In other embodiments the dosage is 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m². In these embodiments the dosage amounts are administered intravenously once every four weeks i.e. 28-day cycle.

Alternatively the dosage amount is between about 10 mg/m² to 45 mg/m². For example, the dosage is between about 11.5 mg/m² to about 12.5 mg/m². Alternatively the dosage is between about 19.5 mg/m² to about 20.5 mg/m², between about 24.5 mg/m² to about 25.5 mg/m², between about 29.5 mg/m² to about 31.5 mg/m², between about 32.5 mg/m² to about 33.5 mg/m², between about 35.5 mg/m² to about 36.5 mg/m², between about 39.5 mg/m² to about 41.5 mg/m², between about 42.5 mg/m² to about 43.5 mg/m², between about 43 mg/m² to about 45 mg/m². In some embodiments, the dosage is about 12 mg/m², about 20 mg/m², about 25 mg/m², about 30 mg/m², about 33 mg/m², about 36 mg/m², about 40 mg/m², about 43 mg/m², or about 45 mg/m². In other embodiments the dosage is 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m² or 45 mg/m². In these embodiments the dosage amounts are administered intravenously once every four weeks i.e. 28-day cycle.

The frequency and timing of administration, and the dosage amounts, can be administered periodically over a cycle of administration to maintain a continuous and/or long term effect of the active agents for a desired length of time. The provided compositions of a NaPi2b-targeted polymer antibody-drug conjugate can be administered hourly, daily, weekly, monthly, yearly or once. The length of time of the cycle of administration can be empirically determined, and is dependent on the disease to be treated, the severity of the disease, the particular patient, and other considerations within the level of skill of the treating physician. The length of time of treatment with a combination therapy provided herein can be one week, two weeks, one months, several months, one year, several years or more.

For example, the frequency of administration of the NaPi2b-targeted polymer antibody-drug conjugate is once a day, every other day, twice weekly, once weekly, once every 2 weeks, once every 3 weeks or once every 4 weeks. The dosage can be divided into a plurality of cycles of administration during the course of treatment. For example, the NaPi2b-targeted polymer antibody-drug conjugate can be administered at the frequency over a period of about a month, 2 months, 3 months, 4 months, 5 months, 6 months, a year or more. The frequency of administration can be the same throughout the period of the cycle or can differ. For example, an exemplary dosage frequency is two times a week at least for a first week of a cycle of administration. After the first week, the frequency can continue at twice a week, can increase to more than twice a week, or can be reduced to no more than once a week. It is within the level of a skilled person to determine the particular dosage frequency and cycle of administration based on the particular dosage being administered, the disease or condition being treated, the severity of the disease or condition, the age of the subject and other similar factors.

If disease symptoms persist in the absence of discontinued treatment, treatment can be continued for an additional length of time. Over the course of treatment, evidence of disease and/or treatment-related toxicity or side effects can be monitored.

The cycle of administration of the NaPi2b-targeted polymer antibody-drug conjugate can be tailored to add periods of discontinued treatment in order to provide a rest period from exposure to the agents. The length of time for the discontinuation of treatment can be for a predetermined time or can be empirically determined depending on how the patient is responding or depending on observed side effects. For example, the treatment can be discontinued for one week, two weeks, three weeks, one month or several months. Generally, the period of discontinued treatment is built into a cycle of dosing regimen for a patient.

An exemplary dosing regimen is a treatment cycle or cycle of administration of 21 days or 28 days. Preferably, the dosing regimen is a treatment cycle or cycle of administration is 28 days. The NaPi2b-targeted polymer antibody-drug conjugate disclosed herein, is administered on day 1, followed by 20 days without dosing or is administered on day 1, followed by 27 days without dosing. It is within the level of one of skill in the art to determine the precise cycle of administration and dosing schedule.

As noted above, the cycle of administration can be for any desired length of time. Hence, the 21-day cycle or 28-day cycle of administration can be repeated for any length of time. For example, the 21-day cycle or 28-day cycle of administration can be repeated for 2 months, 3, months, 4 months, 5, months, 6 months, 7 months, 8 months, 9 months, 10 months, 11 months, 12 months, 1.5 years, 2 years, 2.5 years, 3 years or more. It is within the level of skill of the treating physician to adopt a cycle of administration and dosing regimen that meets the needs of the patient depending on personal considerations specific to the patient and disease to be treated.

Measurement of NaPi2b Expression

In various aspect the invention provides a method for identifying a cancer patient amenable to NaPi2b targeted therapy or monitoring the treatment regimen by measuring the status of NaPi2b expression in a tumor sample obtained from the patient.

In some embodiments, the NaPi2b diagnostic tests can be used to identification subjects for treatment with the NaPi2b targeted polymer drug conjugate.

The sample is derived from the subject having a cancer. The sample of cancer cells is dissected from tissue removed or obtained from the subject. In some embodiments, the sample is a fresh, frozen or an archival biopsy sample.

In some embodiments, the test cell population is derived from fresh, unfrozen tissue from a biopsy sample. In other embodiments, the test cell population is derived from a primary or metastatic site. In some embodiments, the test cell population is derived from a fresh or frozen tissue from a biopsy or surgical sample or ascetic fluid or pleural fluid. In some embodiments, the test cell population is derived from a fixed tissue (e.g., formalin fixation or formalin-fixed paraffin-embedded (FFPE)) from a biopsy or surgical sample or cell block derived from a fluid specimen. The tissue sample may be frozen or fresh.

The requisite level of NaPi2b expression may be that which is identified by the any methods known in the art and more specifically by the methods described herein. For example, the level of NaPi2b expression can be measured by conducting a known immunological assay, such as an enzyme immunoassay, radioimmunoassay, competitive immunoassay, double antibody sandwich assay, fluoroimmuno assay, ELISA, Western blotting technique, agglutination assay, cytofluorometry (e.g. flow cytometry), Fluorescence in situ hybridization (FISH), colorimetric or immunohistochemical staining assay (IHC) for protein expression using an antibody that specifically recognizes NaPi2b. Cell-based assays, such as, for example, flow cytometry (FC), immuno-histochemistry (IHC), RNA expression analysis or immunofluorescence (IF) are particularly desirable in determining NaPi2b expression status, since such assay formats are clinically-suitable.

Flow cytometry (FC) may be employed to determine cell surface expression of NaPi2b in a tumor sample before, during, and after treatment with a drug. For example, tumor cells may be analyzed by flow cytometry for NaPi2b expression, as well as for markers identifying cancer cell types, etc., if so desired. Flow cytometry may be carried out according to standard methods. See, e.g. Chow et al., Cytometry (Communications in Clinical Cytometry) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with NaPi2b-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed NaPi2b in the tumor.

Immunohistochemical (IHC) staining may be also employed to determine the expression of NaPi2b in a tumor sample before, during, and after treatment with a drug. IHC may be carried out according to well-known techniques. See, e.g., ANTIBODIES; A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary polypeptide antibody and secondary antibody; and finally detecting using ABC avidin/biotin method according to manufacturer's instructions.

Immunofluorescence (IF) assays may be also employed to determine the expression of NaPi2b tumor sample before, during, and after treatment with a drug. IF may be carried out according to well-known techniques. See, e.g., J. M. Polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against polypeptide followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (phospho-AKT, phospho-Erk 1/2) and/or cell marker (cytokeratin) antibodies.

In a preferred embodiment the expression of NaPi2b in a sample from a tumor is determined immunohistochemically. In another embodiment, the expression of NaPi2b in a sample from a tumor is determined immunohistochemically (IHC) using the method described in U.S. Ser. No. 16/136,706, which is incorporated herein in its entirety by reference.

Alternatively, the assay may include preparing RNA from the sample, optionally for use in PCR (polymerase chain reaction) or other analytical methodology. The PCR methodology is optionally, for example, RT-PCR (reverse transcription-PCR) or quantitative PCR, such as, for example, real-time RT-PCR, RNA seq and the like. Alternatively, the assaying may be conducted by use of an array, such as a microarray as known in the relevant field, such as, for example, nanostring technologies.

Patients are identified as being responsive to treatment, wherein the treatment is monitored or cancer is detected by detecting and/or measuring the expression level of NaPi2b in a sample.

The detection/measurement of the expression level of NaPi2b is determined by calculating a NaPi2b score. The NaPi2b score is quantitative or semi quantitative. For example detection is scored pathologically to arrive at a pathology score. It is contemplated that any scoring methods known in the art may be used in the methods of the invention. In particular, any histological scoring methods known in the art.

The methods for assessing the measurement results obtained by immunohistochemical staining assays include, for example, the H-score method. The H-score is determined by the following calculation formula (Am J Clin Pathol. 1988; 90 (3): 233-9). H-Score=((% at <1+)×0)+((% at 1+)X 1)+((% at 2+)×2)+((% at 3+) X3) where staining intensity 0 is unstained; staining intensity 1 is weak staining; staining intensity 2 is moderate staining; and staining intensity 3 is strong staining.

In assessment by the H-score method, only cancer cell portions are used. For negative or positive controls for staining intensity, formalin-fixed paraffin-embedded cell lines or xenografts (lines whose protein expression levels are known in advance) may be employed. When there are no control specimens, a plurality of specimens are assessed simultaneously to confirm the overall distribution of staining intensity of the specimens, and then staining intensity may be set.

In addition to the H-score method, other scoring methods known in the art, such as, for example, the Allred method (Harvey, et al. Journal of Clinical Oncology 17, No. 5 (May 1999) 1474-1474), can also be used. Cut-off points are required to be set in each method. Allred score=score of percentage of positive cells+staining intensity score.

The disclosure also provides kits and/or methods for identifying or otherwise refining, e.g., stratifying, a patient population suitable for therapeutic administration of a NaPi2b-targeted antibody-drug conjugates disclosed herein by identifying the NaPi2b score of the subject prior to treatment with a NaPi2b-targeted antibody-drug conjugate disclosed herein. In some embodiments, the test cell population is derived from fresh, unfrozen tissue from a biopsy sample. In some embodiments, the test cell population is derived from a primary or metastatic site. In some embodiments, the test cell population is derived from a frozen tissue from a biopsy or surgical sample or ascetic fluid or pleural fluid. In some embodiments, the test cell population is derived from a fixed tissue (e.g., formalin fixation) from a biopsy or surgical sample. The IHC test measures the amount of NaPi2b receptor protein on the surface of cells in a cancer tissue sample Definitions Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "NaPi2b" (also known as sodium-dependent phosphate transport protein 2B, SLC34A2, NaPiIIb, Npt2, Na(+)-dependent phosphate cotransporter 2B; sodium/phosphate cotransporter 2B; Na(+)/Pi cotransporter 2B; NaPi3b; solute carrier family 34 member 2), when used herein, refers to human NaPi2b (e.g., GenBank Accession No. 095436.3) and includes any variants, isoforms and species homologs of NaPi2b which are naturally expressed by cells, including tumor cells, or are expressed on cells transfected with the NaPi2b gene. These terms are synonymous and may be used interchangeably.

As used herein, the term "NaPi2b antibody" or "anti-NaPi2b antibody" is an antibody which binds specifically to the extracellular region of SLC34A2.

When used herein in the context of two or more antibodies, the term "competes with" or "cross-competes with" indicates that the two or more antibodies compete for binding to NaPi2b, e.g., compete for NaPi2b binding in any art-recognized assay. An antibody "blocks" or "cross-blocks" one or more other antibodies from binding to NaPi2b if the antibody competes with the one or more other antibodies 25% or more, with 25%-74% representing "partial block" and 75%-100% representing "full block", as determined using any art-recognized assay. For some pairs of antibodies, competition or blocking in any art-recognized assay is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal and chimeric antibodies.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. mAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

The term "polypeptide" is used herein as a generic term to refer to native protein, fragments, or analogs of a polypeptide sequence. Hence, native protein fragments, and analogs are species of the polypeptide genus. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences.

Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Green, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —$CH$=$CH$-(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally, whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Polymeric Carrier or scaffold": The term polymeric carrier or scaffold, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Drug": As used herein, the term "drug" refers to a compound which is biologically active and provides a desired physiological effect following administration to a subject in need thereof (e.g., an active pharmaceutical ingredient).

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight of the unmodified polymer unless otherwise specified.

As used herein, "dosing regimen" or "dosage regimen" refers to the amount of agent, for example, the composition containing an NaPi2b-targeted polymer antibody-drug conjugate, administered, and the frequency of administration. The dosing regimen is a function of the disease or condition to be treated, and thus can vary.

As used herein, "frequency" of administration refers to the time between successive administrations of treatment. For example, frequency can be days, weeks or months. For example, frequency can be more than once weekly, for example, twice a week, three times a week, four times a week, five times a week, six times a week or daily. Frequency also can be one, two, three or four weeks. The particular frequency is a function of the particular disease or condition treated. Generally, frequency is more than once weekly, and generally is twice weekly.

As used herein, a "cycle of administration" refers to the repeated schedule of the dosing regimen of administration of the enzyme and/or a second agent that is repeated over successive administrations. For example, an exemplary cycle of administration is a 28 day cycle with administration twice weekly for three weeks, followed by one-week of discontinued dosing. A preferred cycle of administration is a 21 day cycle with administration once every 21 days (i.e., 3 weeks) or a 28 day cycle with administration once every 28 days (i.e., 4 weeks)

As used herein, when referencing dosage based on mg/kg of the subject, an average human subject is considered to have a mass of about 70 kg-75 kg, such as 70 kg and a body surface area (BSA) of 1.73 m$^2$.

As used herein, amelioration of the symptoms of a particular disease or disorder by a treatment, such as by administration of a pharmaceutical composition or other therapeutic, refers to any lessening, whether permanent or temporary, lasting or transient, of the symptoms or, adverse effects of a condition, such as, for example, reduction of adverse effects associated with or that occur upon administration of an NaPi2b-targeted polymer antibody-drug conjugate.

As used herein, when referencing dosage based on "body surface area" (BSA; m$^2$) is the measured or calculated surface area of a human body. For many clinical purposes BSA is a better indicator of metabolic mass than body weight because it is less affected by abnormal adipose mass. Various calculations have been published to arrive at the BSA without direct measurement. In the following formulae, BSA is in m$^2$, W is mass in kg, and H is height in cm. The most widely used is the Du Bois, Du Bois formula: BSA=$0.007184 \times W^{0.425} \times H^{0.725}$. Other methods of determining BSA include for example, the Mosteller, Haycock, Gehan and George, Boyd, Fujimoto, Takahira, Shuter and Aslani or Schlich formulas As used herein, "treating" or "treat" describes the management and care of a patient for the purpose of combating a disease, condition, or disorder and includes the administration of a conjugate of the disclosure, or a pharmaceutical composition thereof in combination with an immunomodulatory therapy, e.g., an immuno-oncology agent such as an immune checkpoint inhibitor, to alleviate the symptoms or complications of a disease, condition or disorder, or to eliminate the disease, condition or disorder.

As used herein, "prevention" or "prophylaxis" refers to reduction in the risk of developing a disease or condition, or reduction or elimination of the onset of the symptoms or complications of the disease, condition or disorder.

The term "effective amount" or "sufficient amount", as it refers to an active agent, refers to the amount necessary to elicit the desired biological response. As used herein, a "therapeutically effective amount" or a "therapeutically effective dose" refers to an amount or quantity of an agent, compound, material, or composition containing a compound that is at least sufficient to produce a detectable therapeutic effect. The effect can be detected by any assay method known in the art. The precise effective amount for a subject will depend upon the subject's body weight, size, and health; the nature and extent of the condition; and the therapeutic selected for administration.

A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "unit dose form" or "unit dosage form" refers to physically discrete units suitable for human and animal subjects and packaged individually as is known in the art.

As used herein, a single dosage formulation refers to a formulation as a single dose.

As used herein, "temporal proximity" refers to that administration of one therapeutic agent (e.g., a NaPi2b-targeted polymer antibody-drug conjugate disclosed herein) occurs within a time period before or after the administration of another therapeutic agent (e.g., an immune checkpoint inhibitor disclosed herein), such that the therapeutic effect of the one therapeutic agent overlaps with the therapeutic effect of the another therapeutic agent. In some embodiments, the therapeutic effect of the one therapeutic agent completely overlaps with the therapeutic effect of the another therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

As used herein a "kit" refers to a combination of components, such as a combination of the compositions herein and another item for a purpose including, but not limited to, reconstitution, activation and instruments/devices for delivery, administration, diagnosis and assessment of a biological activity or property. Kits optionally include instructions of use.

The present disclosure is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present disclosure is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

OTHER EMBODIMENTS

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples are illustrative and are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

AF-HPA Auristatin F-hydroxypropyl amide
BSA Body surface area
CR Complete response
DCR Disease control rate
DES Dose escalation
DLT Dose limiting toxicity
EXP Cohort expansion
IHC Immunohistochemistry
IV Intravenous
MTD Maximum tolerated dose
NSCLC Non-small cell lung cancer
ORR Objective response rate
PBS Phosphate buffered saline
PE Physical examination
PHF poly(1-hydroxymethylethylene hydroxylmethylformal)
PR Partial response
RP2D Recommended Phase 2 dose
SD Stable disease
SRC Safety Review Committee
SRM Safety Review Meeting
TRAE Treatment-related adverse events General Information XMT-1536 was prepared as described in US Application No. 2017/0266311.

AF-HPA was prepared as described in U.S. Pat. No. 8,808,679(B2)

CDRs were identified by the Kabat numbering scheme.

Example 1: Assessment of Safety and Tolerability of XMT-1536

Study Design

The study presented herein is an open label, multi-center Phase 1b study of XMT-1536 administered as an intravenous infusion once every three or four weeks. The dose escalation (DES) part of the study will establish the maximum tolerated dose (MTD) or recommended Phase 2 dose (RP2D) for XMT-1536 in patients with a number of tumor types likely to express NaPi2b, with a focus on patients with platinum-resistant ovarian cancer and non-squamous non-small cell lung cancer (NSCLC). The MTD is defined as the highest dose of XMT-1536 that does not cause unacceptable toxicities defined by the protocol-specific dose limit-toxicity criteria. The RP2D may differ from the MTD and may take into account tolerability, pharmacokinetic and pharmacodynamic measures, and efficacy of XMT-1536 based on RECIST 1.1. After the first cycle, patients may continue to receive XMT-1536 until disease progression provided the drug is well-tolerated and patients continue to derive clinical benefit in the opinion of the Investigator. The DES segment of the study utilized an accelerated titration design. The first 3-week cycle of treatment constitutes the dose limiting toxicity (DLT) evaluation period. For the first two dose levels, a minimum of 1 patient was treated at each dose level. If this patient experiences a treatment-emergent adverse event of Grade 2 or higher, 2 additional patients will be added at this dose level, and the study will subsequently follow a 3+3 design, as described below. If this patient does not experience a Grade 2 or higher treatment-related event or a DLT during the DLT evaluation period, and the Safety Review Committee (SRC) agrees this was a reasonably well-tolerated dose, enrollment will commence at the next dose level. Starting with Dose Level 3, the study will follow a standard 3+3 design, with 3 patients enrolled initially at each dose level. If none of the 3 patients experiences a DLT during the evaluation period and the SRC agrees this was a reasonably well tolerated dose, 3 patients will be enrolled at the next dose level. However, in the event of 1 DLT, 3 additional patients will be enrolled at the same dose level. Any dose level with 2 or more DLTs will be considered to exceed the MTD and subsequent patients will be enrolled at lower dose level(s). After the first cycle, patients may continue to receive XMT-1536 until disease progression if the drug is well-tolerated and patients continue to derive clinical benefit in the opinion of the Investigator.

After completion of DES, the EXP segment of the study will be opened in three cohorts of patients. Cohort 1 will contain patients with platinum-resistant ovarian cancer. Cohort 2 will contain patients with non-squamous NSCLC. Cohort 3 will contain patients with papillary thyroid carcinoma, endometrial carcinoma, papillary renal cell carcinoma, or salivary duct carcinoma.

After an August 2018 protocol amendment, each cycle will be 4-week (28 day) dose cycle. The first two, 4-week cycles of treatment (56 days) constitutes the dose limiting toxicity (DLT) evaluation period. Beginning with this amendment, up to 10 patients will be enrolled for evaluation at 20.0 mg/m$^2$ under the new 4-week cycle dose regimen. If that dose is cleared by the SRC, subsequent dose groups will follow a modified 3+3 design. Three patients will be enrolled initially and if toxicity issues arise, the SRC will review all pertinent data and may decide to add more patients to fully evaluate a dose in question and/or lower the dose. If the dose is well tolerated and 3 patients reach the end of Cycle 2 without DLTs, the SRC may clear this dose and open the next dose. The observation period for DLTs is 56 days, between Day 1 through the end of Cycle 2 which includes the pre-dose assessments before receiving the Cycle 3 dose. A maximum of ten patients will be enrolled per dose level prior to the SRM. that will be conducted no later than 5 days after at least the sixth patient dosed in each level has completed Cycle 2, Day 28 evaluations. The data available for the patients dosed in all prior will be factored into the data review for each applicable dose escalation SRM. Any dose level with 2 or more DLTs occurring in 6 or fewer treated patients will be considered to exceed the MTD and subsequent patients will be enrolled at lower dose level(s). After the second cycle, patients may continue to receive XMT-1536 until disease progression if the drug is well-tolerated and patients continue to derive clinical benefit in the opinion of the Investigator. After completion of DES, the EXP segment of the study will be opened.

All adverse events will be graded according to the National Cancer Institute (NCI) Common Terminology Criteria version (CTCAE v4.03). The observation period for DLTs is 56 days, between Day 1 through end of Cycle 2 which includes the pre-dose assessments before receiving the Cycle 3 dose. In general, adverse events Grade ≥3 are DLTs with modifications for the following criteria: neutropenia hematologic toxicities, gastrointestinal toxicities, hepatic toxicities, and electrolyte imbalances. XMT-1536-related toxicity that delays initiation of Cycle 3 by more than 2 weeks, hospitalization to treat an infusion-related reaction, and any toxicity that prompts modification of the dose to be administered in Cycle 3 are also DLTs. Blood sampling will be performed to determine plasma PK parameters of XMT-1536, its release product auristatin F-HPA, and select metabolites. Testing for anti-drug antibodies (ADA) and neutralizing antibodies (nAb) will be performed. Tumor responses will be Investigator-assessed using Response Evaluation Criteria in Solid Tumors (RECIST), version 1.1, at the end of Cycle 2 and every 2 cycles thereafter.

Study Visits

Study visits will occur. The last day of the current cycle can be the same day as the start of the next cycle throughout the study provided the results from the End of Cycle safety assessments are obtained and reviewed prior to initiating dosing in the next cycle. The Investigator can make an accommodation in the visit schedule based on a patient's medical needs. Discuss potential schedule alterations with the Medical Monitor prior to implementing any adjustment unless it is an emergent need. The Investigator will evaluate every patient prior to initiating a dose of XMT-1536 as described in the Schedule of Assessments. A full physical examination (PE) consists of examining head/ears/eyes/nose/throat (HEENT), palpable tumors, neurological and muscular systems, pulmonary and cardiovascular systems, abdomen and lower extremities. A brief physical examination consists of examining: HEENT, pulmonary and cardiovascular systems. Patients will be evaluated for the occurrence or new and/or worsening toxicities at every visit. All adverse events will be graded according to the National Cancer Institute (NCI) Common Terminology Criteria version (CTCAE v4.03).

Number of Subjects

The exact number of patients to be enrolled in DES cannot be known prospectively and is dependent upon when the MTD or RP2D is attained. Based on preclinical animal studies, it is reasonable to expect a range of 21 to 40 patients to be dosed in DES. The EXP segment of the study is planned to treat up to 30 patients each in 3 disease cohorts. Given drop-out rates, it is reasonable to expect a range of 90 to 105 patients will be dosed in EXP.

Eligibility

Patients who are candidates for enrollment into the study are evaluated for eligibility by the Investigator to ensure that the inclusion and exclusion criteria have been satisfied and that the patient is eligible for participation.

TABLE 1

Inclusion Criteria for DES and EXP

| No. | Eligibility Criteria |
|---|---|
| 1 | Females and males, age ≥18 years old. |
| 2 | ECOG performance status 0 or 1. |
| 3 | Measurable disease as per RECIST, version 1.1. |
| 4 | Resolution of all acute toxic effects of prior therapy or surgical procedures to Grade ≤1 (except alopecia). |
| 5 | Cardiac left ventricular ejection fraction (LVEF) ≥50% or the institution's lower limit of normal by either Echo or MUGA scan. |
| 6 | Adequate organ function as defined by the following criteria: absolute neutrophil count (ANC) ≥1500 cells/mm$^3$, platelet count ≥100,000 cells/mm$^3$, hemoglobin ≥9 g/dL, INR, activated partial thromboplastin time (aPTT), and prothrombin time (PT) all within the institutional upper limit of normal (ULN), serum creatinine ≤1.5 mg/dL or calculated creatinine clearance ≥60 mL/min[1], total bilirubin ≤ ULN, aspartate aminotransferase (AST or SGOT) and alanine aminotransferase (ALT or SGPT) ≤1.5 times the institutional upper limit of normal (ULN).albumin ≥3.0 g/dL. [1]Calculated by Cockroft and Gault method. Creatinine clearance (mL/min) = (140-age) × weight (kg)/72 × (serum creatinine in mg/dL) = mL/min (for females, multiply results by 0.85). |
| 7 | Confirmed availability (prior to Cycle 1, Day 1) of tumor tissue blocks (strongly recommended) or freshly cut tissue slides (See Lab Manual) for NaPi2b testing and exploratory assessments. Tissue specimens must be submitted within 45 days after the first dose of study drug. |
| 8 | For women of childbearing potential and men with partners of childbearing potential, agreement to use a highly effective form of hormonal contraception or two effective forms of non-hormonal contraception by the patient and/or partner, and to continue the use of contraception for the duration of study treatment and for at least 6 months after the last dose of study treatment. Male patients whose partners are pregnant should use condoms for the duration of the pregnancy. |
| 9 | Able to sign informed consent. |

Prophylactic transfusion of blood (or blood components) prior to initial dosing cannot be used to meet enrollment criteria. Transfusion of blood (or blood components) to manage treatment-emergent anemia or other cytopenias is permissible and should be recorded as a concomitant medication. Growth factor prophylaxis cannot be used prior to XMT-1536 administration in any cycle.

TABLE 2

Disease specific inclusion criteria for DES

| No. | Eligibility Criteria |
|---|---|
| 1 | Histologically or cytologically confirmed solid tumors of the types specified below, with incurable, locally advanced or metastatic disease that has failed standard therapy or for which no standard treatment option exists: Platinum-resistant ovarian cancer (including epithelial ovarian cancer, such as, high grade serous ovarian cancer, fallopian tube, and primary peritoneal cancer), Nonsquamous NSCLC, Papillary thyroid carcinoma, Endometrial carcinoma (excluding carcinosarcoma and stromal tumors), Papillary renal cell carcinoma, Salivary duct carcinoma. |

TABLE 3

Disease specific inclusion criteria for expansion segment (EXP)

| No. | Eligibility Criteria |
|---|---|
| | Cohort 1: Platinum-resistant ovarian cancer |
| 1 | Histological diagnosis of high-grade serous ovarian, epithelial ovarian, fallopian tube, or primary peritoneal cancer, excluding the mucinous subtype. |
| 2 | Platinum resistance, defined as disease progression within 6 months of completing a platinum-containing chemotherapy regimen. |
| 3 | No more than 3 lines of prior therapy |
| | Cohort 2: Nonsquamous NSCLC |
| 1 | Adenocarcinoma histological diagnosis of nonsquamous NSCLC |
| 2 | Prior treatment with a platinum-based (cisplatin or carboplatin) regimen and a PD-1 or PD-L1 monoclonal antibody (either in combination or sequentially). |
| 3 | Patients with known oncogenic mutations for which there are approved therapies (e.g. ALK translocation, EGFR mutation) must have documented intolerance or disease progression for the approved therapies for their mutation. Patients must have received prior treatment with a platinum-based regimen, but prior treatment with a PD-1 or PD-L1 monoclonal antibody is not required. |
| 4 | No prior treatment with a cytotoxic agent or immunotherapy. |
| | Cohort 3: Additional indications |
| 1 | For papillary thyroid carcinoma patients, the following are required: (a) progressive, radioactive iodine-refractory, loco-regional recurrent or metastatic disease and (b) resistance or intolerance to prior kinase inhibitor therapy (e.g., lenvatinib, sorafenib). A patient who is considered inappropriate for kinase inhibitor therapy may be enrolled with approval of the Medical Monitor. |
| 2 | For endometrial carcinoma patients, the following are required: (a) a diagnosis of epithelial endometrial carcinoma is required. Stromal tumors and carcinosarcoma (mixed malignant Mullerian tumor) are excluded and (b) a patient must have received at least one prior chemotherapeutic regimen for endometrial cancer with carboplatin/paclitaxel or a similar regimen. Patients should have received prior hormonal therapy for endometrial cancer if appropriate, e.g., for low-grade, hormone receptor-positive endometroid adenocarcinoma. |
| 3 | For papillary renal cell carcinoma patients, the following are required: (a) documented local confirmation of renal cell carcinoma with a predominantly papillary growth pattern and (b) Progression after standard systemic therapy. |
| 4 | For salivary duct carcinoma patients, the following are required: (a) a histologic diagnosis of salivary duct carcinoma (other subtypes of salivary gland cancer are excluded) and (b) progression after standard systemic therapy or a lack of available effective therapy, in the assessment of the investigator. |

TABLE 4

Exclusion Criteria for Dose Escalation and Expansion

| No. | Eligibility Criteria |
|---|---|
| | Exclusion Criteria for Dose Escalation and Expansion |
| 1 | Major surgery within 28 days of starting study treatment; -or- systemic anti-cancer therapy within the lesser of 28 days or 5 half-lives of the prior therapy before starting study treatment (14 days or 5 half-lives for small molecule targeted therapy); -or- recent radiation therapy with unresolved toxicity or within a time window of potential toxicity (consultation with Medical Monitor is recommended). |
| 2 | Brain metastases that: are untreated, are progressive, or have required any type of major treatment, e.g., whole brain radiation treatment, adjuvant chemotherapy, gamma knife, to control symptoms from brain metastases within 30 days of the first study treatment, or any history of leptomeningeal metastasis. |
| 3 | Current known active infection with HIV, hepatitis B virus (HBV), or hepatitis C virus (HCV). In addition, negative serology is required during screening for HBV and HCV: a. HBV: Patients must be negative for hepatitis B surface antigen (HBsAg) and hepatitis B core antibody (anti-HBc). Patients with evidence of prior HBV infection (positive anti-HBc and negative HBsAg) must be negative for HBV DNA to be eligible. b. HCV: Patients must be negative for HCV antibody, or if HCV antibody is positive, patients must have a negative PCR test for HCV RNA. |
| 4 | Current severe, uncontrolled systemic disease (e.g., clinically significant cardiovascular, pulmonary, or metabolic disease) or intercurrent illness that could interfere with per-protocol evaluations. |
| 5 | History of cirrhosis, hepatic fibrosis, varices, or other clinically significant liver disease. Fibroscan testing may be required for patients with a history of chronic liver disease, e.g., fatty liver. Patients with a regular alcohol intake of more than one drink per day for women or more than two drinks today for men are not eligible, and alcohol consumption during trial participation should be discouraged |
| 6 | Patients cannot receive drugs associated with hepatotoxicity concurrent with XMT-1536 administration or for 21 days after the last dose of XMT-1536. Patients may receive acetaminophen/paracetamol for a limited time but at a total daily dose of ≤2 g per day. Use of NSAIDs or steroids for treatment of fever is encouraged. |
| 7 | Severe dyspnea at rest due to complications of advanced malignancy, or requiring supplementary oxygen therapy. |
| 8 | Currently active pneumonitis or interstitial lung disease |
| 9 | Pregnant or nursing women. |
| 10 | Diagnosis of a second malignancy that is likely to require systemic anticancer treatment. |
| 11 | Active corneal or conjunctival disease, or history of corneal or conjunctival disease within 12 months prior to enrollment. |
| 12 | Use of strong CYP450 inhibitors. |
| | Exclusion Criterion for Expansion |
| 10 | Use of strong CYP450 inhibitors. |

Use of Drugs Associated with Hepatotoxicity

Drugs Categorized by the FDA of those drugs most likely to possibly cause drug-induced liver injury (DILI) should not be used during study participation. An exception for the use of paracetamol (acetaminophen) is described in Exclusion Criterion 6. If a drug on the FDA list must be used during the study to render appropriate medical care and for which no alternative is available the Medical Monitor needs to discuss the circumstance.

Subject Withdrawal Criteria

A patient is free to withdraw from the study at any time. Patients who wish to terminate study participation early will be requested to continue general medical follow-up through at least 30 days post-dose for safety monitoring purposes, if possible. Entrance into hospice care preempts this request. Procedures described for the End of Treatment visit will be followed.

In all cases, the reason for withdrawal must be recorded in the eCRF. If the reason is initially unknown, the patient should be followed to establish whether the reason was an adverse event. If yes, this event will be recorded as the reason for study termination.

Dose and Administration

XMT-1536 is provided as a colorless to yellow or brown liquid in a 5 mL round, flint glass tubing vial with a gray chlorobutyl rubber stopper with a barrier film covered by a 20 mm aluminum, green flip-off cap. Each single-use vial contains 2.5 mL of XMT-1536 antibody drug conjugate at a concentration of 10 mg/mL and pH of 4.0 to 6.0.

Vials must be stored at −20° C. (±5° C.) in a secure, temperature-controlled freezer. XMT-1536 vials are inventoried and controlled using the institution's standard pharmacy procedures for control of a research substance. The assigned CRA will review storage conditions and the maintenance of these conditions during periodic on-site visits.

Each XMT-1536 individual vial will be allowed to thaw at room temperature for up to 60 min before preparing a patient's dose. Inspect thawed vials before use: the liquid should be clear to yellow to brown with essentially no visible particulates. Vials must not be shaken or placed in direct sunlight. Once the dose for infusion has been prepared, it can be retained at room temperature, under typical room lighting conditions, for a maximum of 4 hours before administration.

XMT-1536 will be administered according to body surface area (BSA). The BSA adjusted dose is calculated following each institution's standard practice. When possible, the Mosteller Formula will be used. The starting dose was calculated based on height and weight collected within 14 days of the first dose (can be collected the day of first dose). Dose adjustments based on subsequent weight measurements are made in accord with each institution's standard practice. If a standard practice does not exist, additional weight measurements are obtained and BSA confirmed or altered prior to dosing at Cycle 2 and every two cycles thereafter.

Each dose is prepared in a 100 mL, 0.9% NS PVC infusion bag. Dose preparation is performed according to Investigational Site procedures. Refer to Pharmacy Manual for detailed instructions. Dose preparation will be documented in each patient's study participation record and follow all institutional practices including quality assurance checks The planned starting dose in the dose escalation part of the study is 3 mg/m² of XMT-1536 ADC. The dose escalation scheme is shown in Table 5 below. As of August 2018, DL 5 (30 mg/m₂) had been cleared by SRC. However, based on emerging safety data, the SRC decided to extend the DLT observation period to two, four week cycles (56 days), amend the inclusion and exclusion criteria, and add additional patients at DL 4 (20 mg/m²), with the intention to resume dose escalation per protocol guidelines if this dose is found to be tolerable. The SRC may decide to: (1) Escalate the dose to the next planned level or a higher dose level that is less than the planned increase based on the data demonstrating drug tolerability. (2) Add up to 3 more patients to a the current dose level for additional evaluation (3) De-escalate to a lower dose level for further evaluation; either a previously stipulated dose level or new lower dose level may be chosen based on patient safety data. (4) MTD has been met and no further dose escalation will occur. At least 6 patients will be treated at the MTD or RP2D before the expansion phase of the study is opened. The SRC may decide to escalate by a smaller increment than shown in Table 5, depending on tolerability of a given dose level and after review of all pertinent patient data for any or all dose levels.

TABLE 5

| Dose Escalation | Start | 100% | 100% | 67% | 50% | 20% | 20% |
|---|---|---|---|---|---|---|---|
| Dose Level (DL) | 1 | 2 | 3 | 4<br>4A | 5<br>5A | 6<br>6A | 7A |
| Initial number of patients | 1 | 1 | 3 | 3 | 3 | 3 | 3 |
| Planned dose, mg/m² | 3 | 6 | 12 | 20 | 30 | 40 (DL 6)<br>36 (DL 6A) | 43 |

The BSA adjusted dose is calculated following each institution's standard practice. When possible, the Mosteller Formula is used. The starting dose is calculated based on height and weight collected within 14 days of the first dose and can be collected on the day of first dose. Dose adjustments based on subsequent weight measurements are made in accord with each institution's standard practice. If a standard practice does not exist, additional weight measurements are obtained and BSA confirmed or altered prior to dosing at Cycle 2 and every two cycles thereafter.

Customary supportive care medications may be used for treatment of concurrent, acute conditions that are associated with dosing, e.g., hypersensitivity reaction, emesis, diarrhea and fever. Prophylactic treatments for infusion reactions or hypersensitivity are not recommended before any patient's first dose but may be administered in advance of the second and/or subsequent doses if these reactions occur after the first dose. Treatment with anti-emetic and anti-pyretic medications may be indicated for several days after infusion, and may be used before the first dose if indicated by the patient's medical history. Dose adjustments after Cycle 1 are permitted under specific circumstances.

The initial dose for each patient is administered over 90 min. If no infusion-related reaction (IRR) occurs, all subsequent doses are administered over 30 to 90 minutes at the discretion of the Investigator. Treatment of IRRs should be according to institutional standards or the study guidelines.

Once a patient completes Cycle 1 (DLT evaluation period) dose adjustments may be made if a patient experiences toxicity but would benefit from further treatment with XMT-1536, in the opinion of the investigator.

Criteria for Continued Dosing

In Cycle 2 and beyond, the Investigator or designee should review End of Cycle/pre-dose clinical and laboratory findings before proceeding with study drug administration. All liver enzymes should have recovered to Grade 1 or lower, or to the patient's baseline, before proceeding. Laboratory data, particularly liver tests, should be compared to the patient's baseline, and delay of dosing (e.g. for 1 week) should be considered to allow for more complete recovery of liver function or to allow resolution of other AEs, e.g. nausea, vomiting, anorexia or fatigue.

Intrapatient Dose Reduction

Once a patient completes Cycle 1, dose adjustments may be made if a patient experiences toxicity but would benefit from further treatment with XMT-1536, in the opinion of the investigator. Treatment at a reduced dose may commence only if the observed toxicity resolves to Gr≤1 or baseline within 21 days or 28 days after the toxicity began, and at the discretion of the Investigator after discussion with the Medical Monitor (Table 6).

The first dose reduction will be to one dose lower than the dose level where the toxicity was observed.

The second reduction will be two doses lower than the original dose at which the toxicity was observed.

If a third dose reduction is necessary the patient will be discontinued.

TABLE 6

Dose Reduction after Completion of Cycle 1

| Dose Reduction | Dose[1] |
|---|---|
| $1^{st}$ | One dose level lower than original dose |
| $2^{nd}$ | Two dose levels lower than original dose |
| $3^{rd}$ | Patient Discontinuation |

[1]The reduced dose cannot be lower than 3 mg/m$^2$ (DL 1)

In Cycle 2 or subsequent cycles, peripheral motor or sensory neuropathy Grade ≥3 that does not resolve to Grade ≤2 within 21 days after occurrence requires dose reduction or termination of treatment. In general, before making any dose adjustments, call the Medical Monitor to discuss.

In Cycle 2 and beyond, the Investigator or designee should review End of Cycle/pre-dose clinical and laboratory findings before proceeding with study drug administration. All liver enzymes should have recovered to Grade 1 or lower, or to the patient's baseline, before proceeding. Laboratory data, particularly liver tests, should be compared to the patient's baseline, and delay of dosing (e.g. for 1 week) should be considered to allow for more complete recovery of liver function or to allow resolution of other AEs, e.g. nausea, vomiting, anorexia or fatigue.

Dose Reductions in DES and EXP Due to Hepatoxicity

Patients in both DES and EXP who experience hepatic transaminase or ALP levels of Grade ≥3 will return to office, be retested within 48 to 72 hours of the initial Grade ≥3 value, and monitored at least weekly until the levels return to Grade ≤1 or to that patient's baseline. If the patient resides a significant distance from the research facility such that return is a hardship, arrangements can be made to have a local blood draw with the results and local normal range returned to the Study Investigator for monitoring.

A patient who experiences one increase in hepatic transaminase or ALP to Grade ≥3 and requires longer than 72 hours to recover to Grade ≤2 (or baseline) may continue dosing in the next cycle but at the next lower dose.

If the patient experiences a second increase in hepatic transaminase or ALP to Grade ≥3 that requires longer than 72 hours to recover to Grade ≤2 (or baseline) after one prior dose reduction, he or she may continue dosing in the next cycle but at the next lower dose than that at which the second elevation occurred.

If the patient experiences a third Grade ≥3 elevation in hepatic transaminase or ALP, that requires longer than 72 hours to recover to Grade ≤2 (or baseline), after two prior dose reductions, he or she will be discontinued from the study and monitored at least weekly until these levels return to Grade ≤1 (or baseline).

XMT-1536 dose will not be modified for an increase in hepatic transaminase or ALP to Grade ≥3 if fewer than 72 hours are required to recover to Grade ≤2 (or baseline).

Any patient who experiences a Gr 4 hepatic transaminase or ALP will discontinue from the study and not undergo dose reduction. The Gr 4 toxicity will be monitored at least weekly until return to Gr≤1 or baseline.

Whether or not the threshold for dose reduction is met, any increase in hepatic transaminase or ALP above Grade 1 must return to Grade ≤1 or baseline before the next dose of study drug.

Duration of Treatment

Treatment will continue indefinitely unless one of the following occurs: disease progression, inter-current illness that prevents further administration of treatment, unacceptable adverse events or pregnancy, patient non-compliance with the protocol, patient withdraws consent for participation from the study, and/or general or specific changes in the patient's condition render the patient unacceptable for further treatment in the judgment of the Investigator.

However, should disease progression occur yet the Investigator perceives the potential for the patient to derive benefit from continued exposure to XMT-1536, the Investigator has the option to continue dosing after discussion with the Medical Monitor.

Primary Objectives

The primary objectives in the Dose Escalation (DES) study is to determine the maximum tolerated dose (MTD) and recommended Phase 2 dose (RP2D) of XMT-1536 administered intravenously once every three or four weeks and assess the safety and tolerability of XMT-1536.

The primary objectives in the expansion study is to assess further the safety and tolerability of XMT-1536 administered at the MTD/RP2D identified in the DES, assess the preliminary anti-neoplastic activity of XMT-1536

Secondary Objectives

The secondary objective in the Dose Escalation (DES) study is to assess the preliminary anti-neoplastic activity of XMT-1536.

The secondary objectives in the DES and expansion studies are to assess the pharmacokinetics (PK) of XMT-1536, its release product, and selected metabolites, assess the development of anti-drug antibodies to XMT-1536, and assess the association of tumor expression of NaPi2b and objective tumor response to XMT-1536.

Exploratory objectives in the DES and expansion studies are to retrospectively evaluate the association of objective response with tumor expression of genes other than NaPi2b, or other tumor molecular features Measurement of Efficacy In both segments of the study assessments with computerized tomography (CT) scans and RECIST version 1.1 criteria are performed at the end of Cycle 2 and at the end of every even-numbered cycle thereafter. Patients are continuously evaluated for adverse events, the use of concomitant medications, and the occurrence of infusion reactions in any cycle. Pharmacokinetic profiles of XMT-1536 and select release products/metabolites and the development of anti-drug antibodies are evaluated. RECIST version 1.1, is used to measure tumor response. The objective response rate (ORR—rate of complete response [CR] and partial response [PR]) and disease control rate (DCR—rate of CR, PR, and stable disease [SD]) will be measured for each cohort. Response duration, progression-free survival (PFS) and overall survival (OS) is estimated.

The primary analysis of efficacy is performed using both DES and EXP data. The primary endpoint is ORR by Investigator radiologic review, and is defined as the proportion of patients who achieve a confirmed PR or CR per RECIST 1.1. A secondary endpoint is the DCR which is defined as the proportion of patients who achieve complete response, partial response, and/or stable disease of any duration per RECIST 1.1. The number and percentage of patients achieving response or clinical benefit is summarized and an exact 95% confidence interval (CI) is provided.

Analysis of other efficacy endpoints including duration of response (DOR), progression-free survival (PFS) and overall survival (OS) are be reported, where ever possible according to standard response criteria. Kaplan-Meier estimates of medians and quartiles with 95% CIs are reported for these statistics.

The efficacy endpoints are analyzed using both the efficacy analysis set and the efficacy evaluable analysis set in each cancer type cohort.

Pharmacokinetics Analysis

The PK profile of the active ingredient of XMT-1536, its release product and selected metabolites are determined for each patient by non-compartmental analysis using standard PK software (e.g., Phoenix WinNonlin). PK parameters per patient include time of maximum observed concentration ($t_{max}$), maximum concentration ($C_{max}$), and area under the concentration curve for the last measurable concentration ($AUC_{0-last}$). When the terminal elimination phase is identified, additional parameters such as elimination half-life, clearance, and volume of distribution are determined.

The handling of missing concentration and covariate data, outliers and values below the limit of quantification as well as details of the modeling for dose-response and PK parameter-response relationships are provided in the PK analysis plan.

Statistical Analysis

A Statistical Analysis Plan (SAP) is written and contain three sections: analysis of data (1) from DES, (2) from EXP, and (3) and combined data from DES and EXP. This SAP will address the analysis of data recorded in the clinical database as well as laboratory data and other data. Each section will be finalized before enrollment in that section has completed and prior to locking the database for the specific study segment, i.e., DES or EXP. Selected tables, listings or figures (collectively referred to as TLFs) after the end of DES and EXP will be generated for review purposes, and will be indicated in the SAP, but no analysis report will be prepared for these intermediate reports. One final analysis report will be created and included in the final Clinical Study. The final TLFs and clinical study report will be prepared after data from both phases have been locked. Any changes made to the SAP for a section after enrollment in that section has been completed will be shared with the Investigators. Any deviations from the planned analysis will be described in the final study report.

Clinical data to PK vendor will be transferred to support PK analysis. A separate analysis plan addressing the PK profile of XMT-1536, its release product and metabolites will be prepared.

Data from DES will be adequately summarized and reviewed with the SRC, at a minimum, before EXP dosing begins. Based on review of DES data, a protocol amendment may be created and submitted for approval prior to initiating the EXP segment. Statistical analyses will be carried out by Novella Clinical using SAS Version 9.3 or higher.

Continuous variables, including baseline characteristics, will be summarized by reporting the number of observations, mean, standard deviation, median, minimum and maximum. Categorical/discrete variables will be summarized using frequency tables showing the number and percentage of patients within a category. Time-to-event data will be summarized using the Kaplan-Meier method.

Unless indicated otherwise, summary statistics will be reported for observed data only. Missing data will not be imputed. If a baseline value is missing, no change from baseline will be calculated. Baseline is defined as the last available observation prior to the first administration of study drug on Cycle 1, Day 1. The handling of missing data will be specified in the SAP along with the methods used for reporting the end points.

Results

As of February 2019, twenty patients have been dosed across 6 dose levels (3 mg/m² to 40 mg/m²), 21-day cycle and sixteen patients across 2 dose levels, (20 mg/m² to 30 mg/m²), 28-day cycle. Thirteen of 20 patients completed the 21-day DLT evaluation period. Sixteen of 16 patients completed the 28-day evaluation period. One DLT occurred in the patient dosed at 40 mg/m², 21-day cycle attributed to study drug and one DLT occurred in the patient dosed at 30 mg/m², 28-day cycle, attributed to study drug. Two SAEs have occurred that were related study drug: congestive heart failure in DL 4, 2 mg/m², 21-day cycle and pyrexia in DL 5, 30 mg/m², 21-day cycle. Treatment-related adverse events (TRAEs) have been Grade 1 or 2; the most common TRAEs to date were anemia, arthralgias, fatigue, vomiting, anorexia, AST increase, diarrhea, dyspnea (unrelated or unlikely related), hypoalbuminema (unrelated or unlikely related), hypoxia (unrelated), headache, nausea, proteinuria and vomiting. Ten patients have had post-treatment restaging scans, with stable disease (SD) as a best response for 9 patients.

As of August, 2019, fifty-one patients have been dosed across 9 dose levels (3 mg/m₂ to 40 mg/m² in a 21-day regimen (n=20) and 20 mg/m² to 36 mg/m² in a 28-day regimen (n=31)). One DLT occurred in one patient dosed at 30 mg/m², 28-day cycle and one DLT occurred in one patient dosed at 36 mg/m², 28-day cycle. Both were considered related to XMT-1536.

Table 7 gives the characterization of the patients enrolled across 6 dose levels (2 to 40 mg/m²), 21-day cycle and 2 dose levels 20 to 30 mg/m²), 28-day cycle.

TABLE 7

| Dose Level | Dose (mg/m²) | Cycle Durations (Days) | Tumor Types N | Age Range Y/o | Duration on Study Min/Max |
|---|---|---|---|---|---|
| 1 | 3 | 21 | N = 1 Ovarian | 55 | 4 cycles |
| 2 | 6 | 21 | N = 1 Ovarian | 54 | 2 cycles |
| 3 | 12 | 21 | N = 7 Ovarian-1 NSCLC-2 Endometrial-3 Papillary Renal-1 | 39 to 67 Mean = 54 Median = 70 | 1 to 4 cycles |
| 4 | 20 | 21 | N = 6 Ovarian-2 NSCLC-1 Endometrial-1 Fallopian Tube-1 Salivary Duct-1 | 58 to 94 Mean = 72 Median = 70 | 1 to 10 cycles |
| 5 | 30 | 21 | N = 4 Ovarian-3 NSCLC-1 | 63 to 68 Mean = 66 Median = 66 | 1 to 4 cycles |
| 6 | 40 | 21 | N = 1 Ovarian Enrollment Complete | 54 | 1 cycle |
| 4A | 20 | 28 | N = 8 Ovarian N = 1 Papillary Renal | 47-74 Mean = 62 Median = 63 | 1 to 6 cycles |
| 5A | 30 | 28 | N = 7 | 51-76 Mean = 68 Median = 71 | 2 to 3 cycles |

The protocol was amended in August, 2018. The 21-day cycle was extended to 28 days and the observation period for DLT evaluation was extended to include two, 28-day cycles. This is the period after which the Safety Review Committee evaluates patients' responses to XMT-1536 and decides if dose escalation should occur. Table 8 is a summary of the patients dosed as of February 2019.

TABLE 8

| Dose Level (DL) | Dosing Regimen | Number of Patients |
| --- | --- | --- |
| DL 1, 3 mg/m$^2$ | 21-day cycle, DLT observation period 1 cycle | 1 |
| DL 2, 6 mg/m$^2$ | 21-day cycle, DLT observation period 1 cycle | 1 |
| DL 3, 12 mg/m$^2$ | 21-day cycle, DLT observation period 1 cycle | 7 |
| DL 4, 20 mg/m$^2$ | 21-day cycle, DLT observation period 1 cycle | 6 |
| DL 5, 30 mg/m$^2$ | 21-day cycle, DLT observation period 1 cycle | 4 |
| DL 6, 40 mg/m$^2$ | 21-day cycle, DLT observation period 1 cycle | 1 |
| DL 4A, 20 mg/m$^2$ | 28-day cycle, DLT observation period 2 cycle | 9 |
| DL 5A, 30 mg/m$^2$ | 28-day cycle, DLT observation period 2 cycle | 7 |

FIG. 1 is a "swimmers plot" that summarizes the details for the time on study for twenty patients though DL6, 21-day cycle (n=19) and four patients dosed in the 28-day cycle (n=4). The plot maps patients by dose level and tumor type on the y axis, against time on study drug on the x axis. The x axis is organized by week time intervals. At lower doses the majority of patients came off study because of progressive disease, but starting at DL4, most patients had stable disease.

Figure 2:
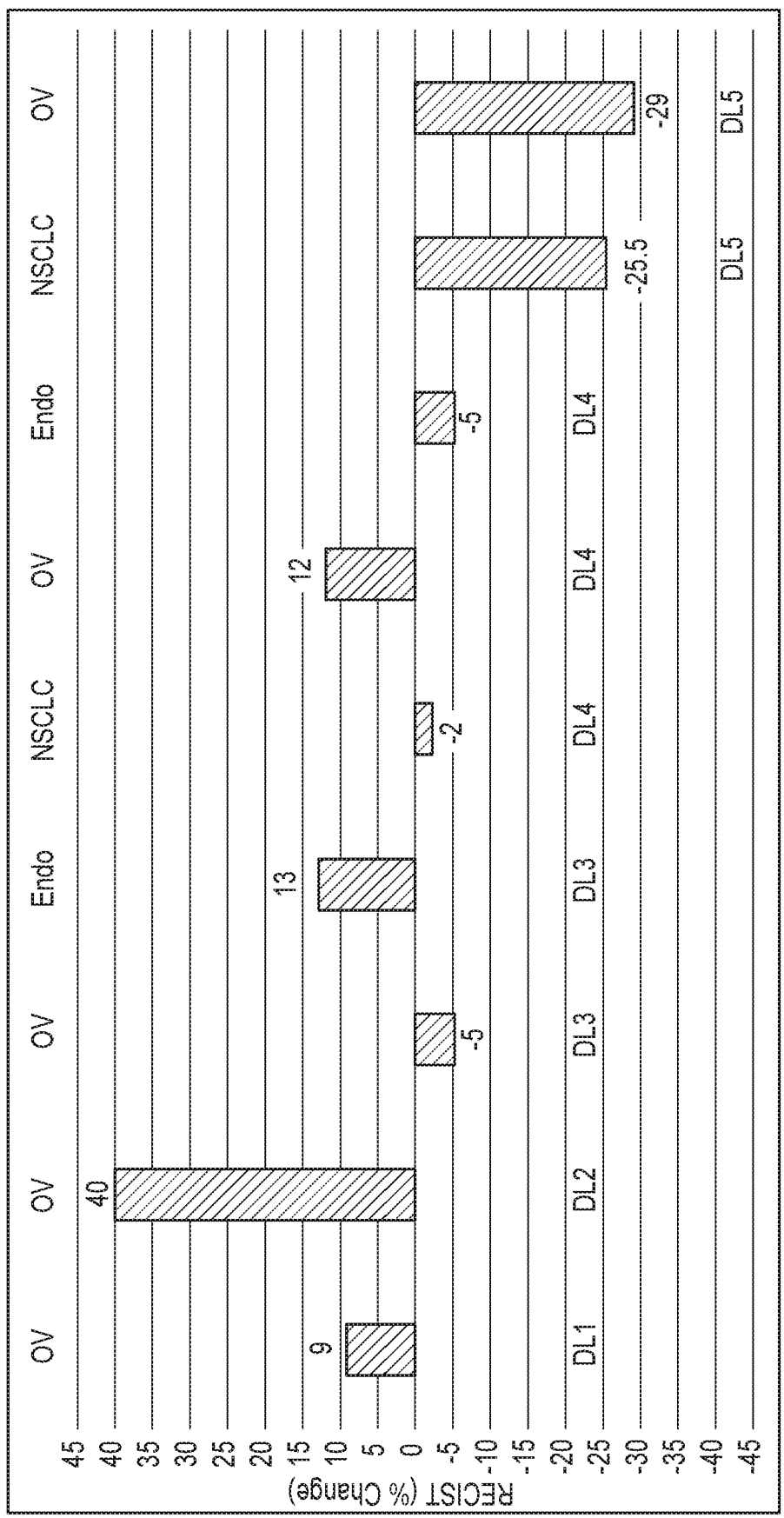
FIG. 2 is a "waterfall plot" that shows the best response by RECIST criteria for the patients in DL1 to DL5 on the 21-day treatment cycle who have had at least one scan to date.

FIG. 2 is a "waterfall plot" that shows the best response by RECIST criteria for the patients dosed in the 21-day cycle and who have had at least one scan to date. The y axis shows change in tumor size by percent. The x-axis organizes the response by dose level. Although the number of patients at each dose is small, there appears to be a dose response. Starting at DL 5, two, ongoing patients reached nearly partial remission (defined as greater than or equal to a 30% reduction in tumor size from baseline).

Figure 3:
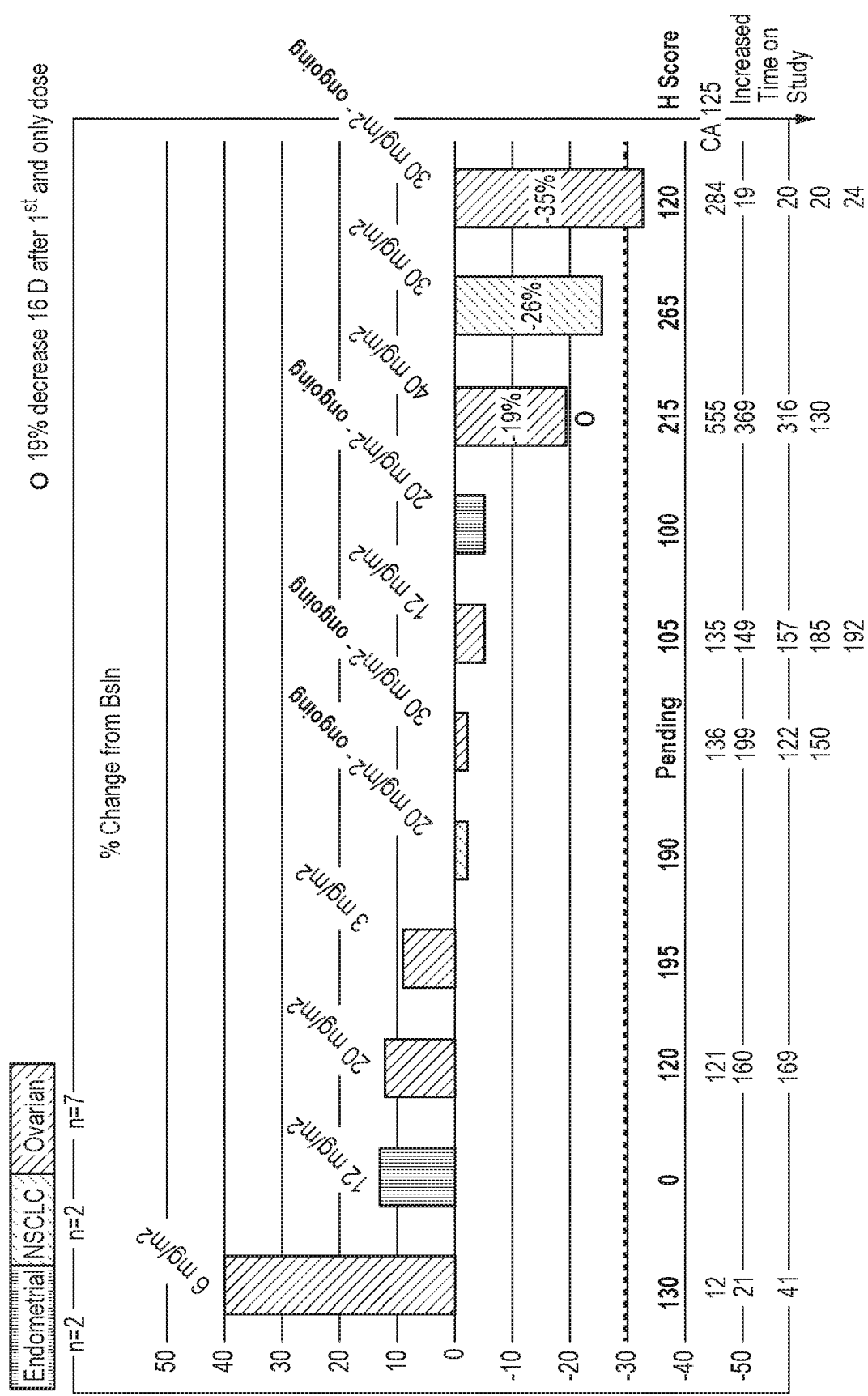
FIG. 3 shows the best overall response for patients (n=11) on the 21-day treatment cycle.

FIG. 3 shows the overall best response for 11 patients as well as the H score and CA-125 levels for the ovarian cancer patients dosed in the 21-day cycle.

Figure 4:
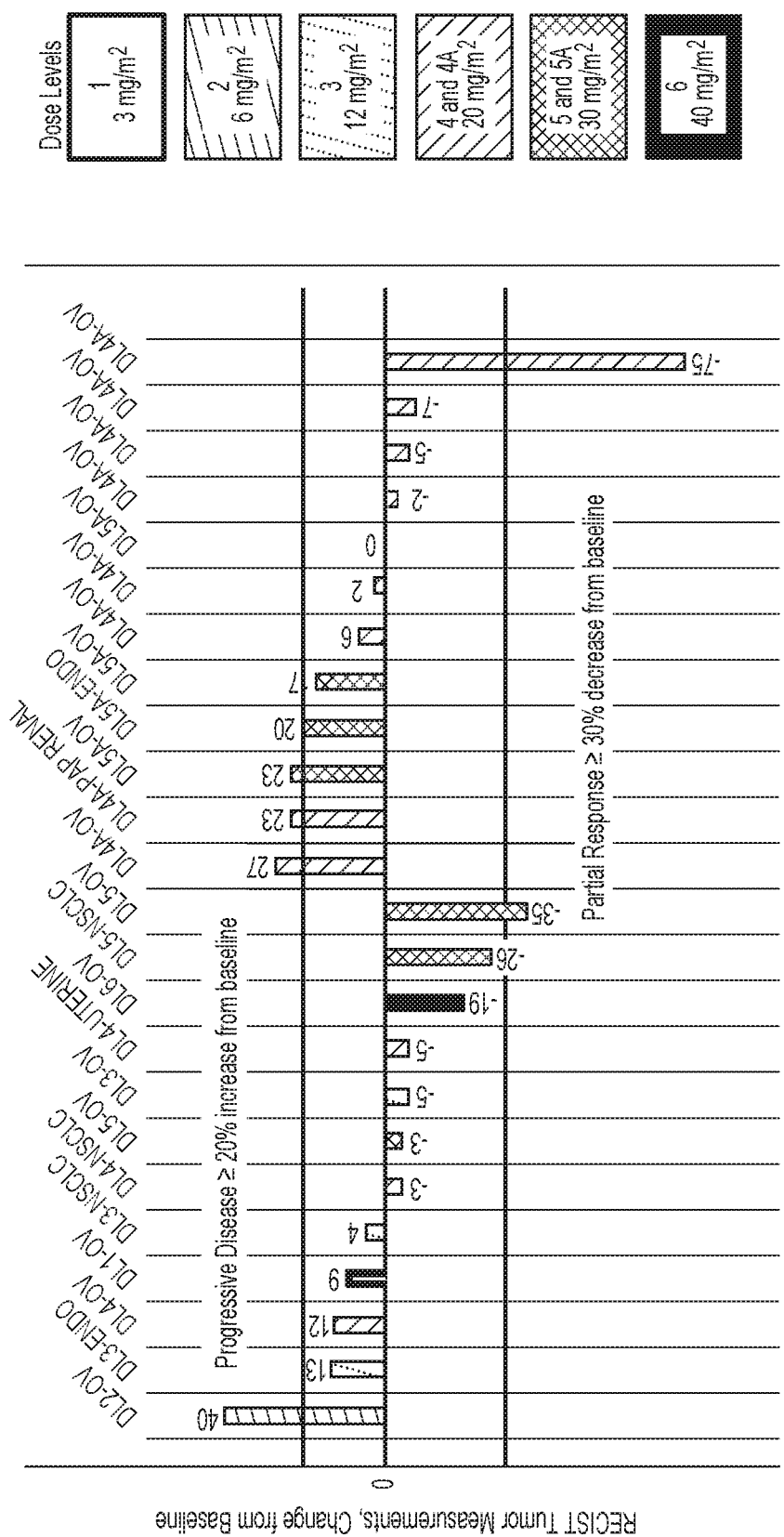
FIG. 4 is a "waterfall plot" that shows the best response by RECIST criteria for the patients dosed in the 21-day cycle and 28-day cycle and who have had at least one scan to date.

FIG. 4 is a "waterfall plot" that shows the best response by RECIST criteria for the patients dosed in the 21-day cycle and 28-day cycle and who have had at least one scan to date. The y axis shows change in tumor size by percent. The x-axis organizes the response by dose level. Although the number of patients at each dose is small, there appears to be a dose response. Starting at DL 5, two patients reached nearly partial remission (defined as greater than or equal to a 30% reduction in tumor size from baseline). At DL 4A, one patient reached partial remission.

Figure 5:
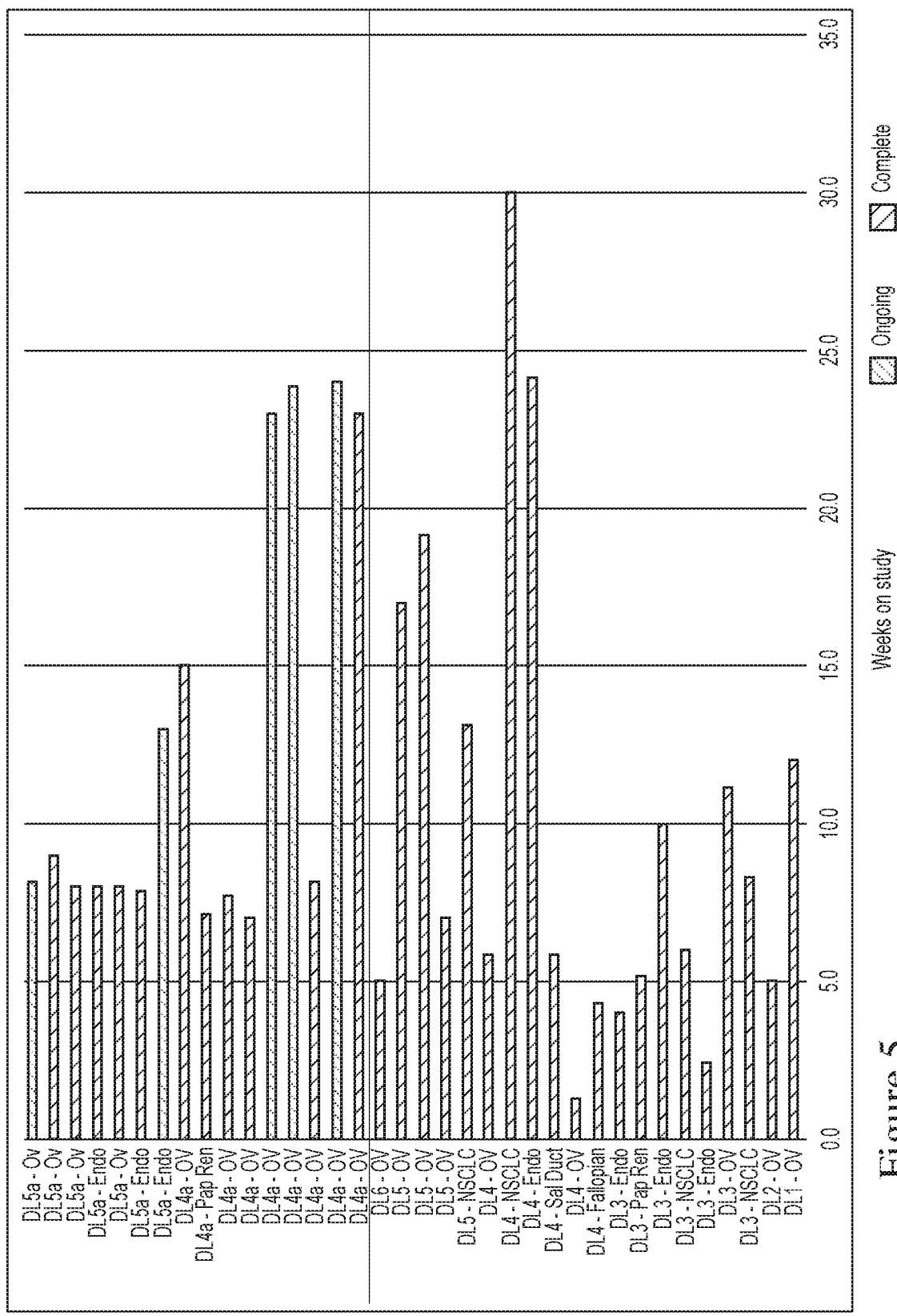
FIG. 5 is a "swimmers plot" that summarizes the details for the time on study for patients though DL6, 21-day cycle (n=20) and DL 4A and DL 5A patients dosed in the 28-day cycle (n=16).

FIG. 5 is a "swimmers plot" that summarizes the details for the time on study for patients though DL6, 21-day cycle (n=20) and DL 4A and DL 5A patients dosed in the 28-day cycle (n-=16). The plot maps patients by dose level and tumor type on the y axis, against time on study drug on the x axis. The x axis is organized by week time intervals. At lower doses the majority of patients came off study because of progressive disease, but starting at DL4, most patients had stable disease.

As of May 10, 2019, thirty-seven patients have been dosed across 6 dose levels (3 mg/m$^2$ to 40 mg/m$^2$), 21-day cycle and seventeen patients across 2 dose levels, (20 mg/m$^2$ to 30 mg/m$^2$), 28-day cycle. Table 9 summarizes the patient characteristics. The treatment was well tolerated with most adverse events being Grade 1 or 2 and no Grade 4 or 5 TRAE being reported. Low rate of toxicities often associated with microtubule-targeting agents or ADCs, such as, for example, neutropenia, ocular toxicities, or peripheral neuropathy was observed.

Table 10 summarizes the TRAE in ≥10% of the patients. Thirteen patients (33%) serious adverse events (SAE) were reported. Two possible treatment related SAEs were Grade 2 pyrexia at DL5 (30 mg/m$^2$) and Grade 3 cardiac failure congestion at DL4 (20 mg/m$^2$), Seventeen SAEs unrelated or unlikely related to treatment occurred in 11 patients: intestinal/small intestinal obstruction (3), disease progression (2), hypoxia (2), pleural effusion (2), abdominal pain, acute blood loss anemia, cellulitis staphylococcal, cerebrovascular accident, hemorrhagic anemia, malignant ascites, pericardial effusion, subdural hematoma, and vaginal hemorrhage. Two dose limiting toxicities were reported at DL 5A (30 mg/m$^2$) and DL 6 (40 mg/m$^2$). At DL 5A, Grade 3 AST was elevated at cycle 1, day 8 and returned to Grade 2 within 7 days and to Grade 1 within 13 days. The AST elevation was accompanied by Grade 1 alkaline phosphatase elevation, but no elevation of ALT or bilirubin was reported. As DL6, Grade 3 AST was elevated at cycle 1, day 8 and returned to Grade 1 within 21 days. The AST elevation was accompanied by Grade 2 ALT elevation which resolved to Grade 1 within 8 days, and Grade 1 alkaline phosphatase elevation but no elevation of bilirubin was reported.

TABLE 9

Patient Characteristics (N = 37)

| Age (years) | Median (range) | 64 (39-93) |
| --- | --- | --- |
| Sex - N (%) | Female | 32 (86) |
|  | Male | 5 (14) |
| ECOG performance status - N (%) | 0 | 11 (30) |
|  | 1 | 26 (70) |
| Tumor type - N (%) | Ovarian, fallopian tube, or primary peritoneal | 22 (59) |
|  | NSCLC | 4 (11) |
|  | Endometrial | 8 (22) |
|  | Papillary renal | 2 (5) |
|  | Salivary duct | 1 (3) |
| Prior lines of therapy for metastatic disease | Median (range) | 4 (1-13) |
| Prior lines of therapy, ovarian cancer only (N = 22) | Median (range) | 5 (1-11) |

TABLE 10

| Preferred Term | Grade 1 | Grade 2 | Grade 3 | Total |
| --- | --- | --- | --- | --- |
| Nausea | 12 (32) | 2 (5) | 0 | 14 (38) |
| Fatigue | 4 (11) | 7 (19) | 0 | 11 (30) |
| Headache | 5 (14) | 5 (14) | 0 | 10 (27) |
| Aspartate aminotransferase (AST) increased | 3 (8) | 2 (5) | 4 (11) | 9 (24) |
| Decreased appetite | 1 (3) | 6 (16) | 0 | 7 (19) |
| Blood alkaline phosphatase increased | 6 (16) | 0 | 0 | 6 (16) |
| Vomiting | 4 (11) | 1 (3) | 0 | 5 (14) |
| Gamma-glutamyltransferase (GGT) increased | 3 (8) | 1 (3) | 0 | 4 (11) |
| Myalgia | 3 (8) | 1 (3) | 0 | 4 (11) |
| Pyrexia | 3 (8) | 1 (3) | 0 | 4 (10) |

The plasma PK profile for the analytes (total antibody; conjugated drug (AF-HPA); free drug (AF-HPA) and the drug metabolite auristatin F (AF)) was determined in blood samples from 30 patients (3 mg/m$^2$, n=1; 6 mg/m$^2$, n=1; 12 mg/m$^2$, n=7; 20 mg/m$^2$, n=15; 30 mg/m$^2$, n=5; 40 mg/m$^2$, n=1). The results normalized to dose, showed that the exposure increased with increasing doses and was nearly dose proportional. The PK characteristics is consistent with that reported for other approved antibody-drug conjugates or those currently in clinical development. There was low systemic expose of free drug (AF-HPA) or its metabolite (AF) compared to that of the conjugated drug. Additionally, there was no accumulation of free drug or its metabolite after administration of multiple doses.

Cut slides or whole tissue blocks from patient tumors, if available, were submitted for IHC expression analysis. Immunohistochemistry was established using an automated TechMate 500 or TechMate 1000 (BioTek Solutions/Ventana medical Systems) platform, where various antigen retrieval conditions and primary antibody titrations were tested to develop a higher through-put protocol. A protocol was selected based on staining of control material and staining of preclinical material with known response to ADC treatment. Briefly, for the established protocol, 4μ sections were cut, dewaxed, and rehydrated through xylene and a series of alcohols. Slides were antigen retrieved in a standard steamer using BioGenex AR-10 retrieval solution. On the TechMate platform, further retrieval was performed with Proteinase K (DAKO). Following serum blocking: the primary antibody (anti-NaPi2b/MERS67) was applied for 30 minutes at room temperature, then endogenous peroxidase block and non-biotin polymer-based detection (rabbit Polink-2 Plus detection system, GBI) was used and finally a brief hematoxylin counterstaining.

Tumor membrane staining was evaluated by manual reading on a light microscope using an "H-Score" method. A hematoxylin and eosin stained slide as well as a rabbit IgG isotype control stained slide were evaluated as part of the scoring process. The same scoring method was used for all evaluated tumor types. The H-score incorporates staining intensity (determined by increasing intensity from 0 to 3+) as well as percent cells positive detected at the tumor cell membrane. H-Score=(% at <1+X 0)+((% at 1+)X 1)+((% at 2+)×2)+((%3+) X3). Hypocellular specimens or those where the primary tumor was not represented in the submitted specimen are not shown.

Figure 6:
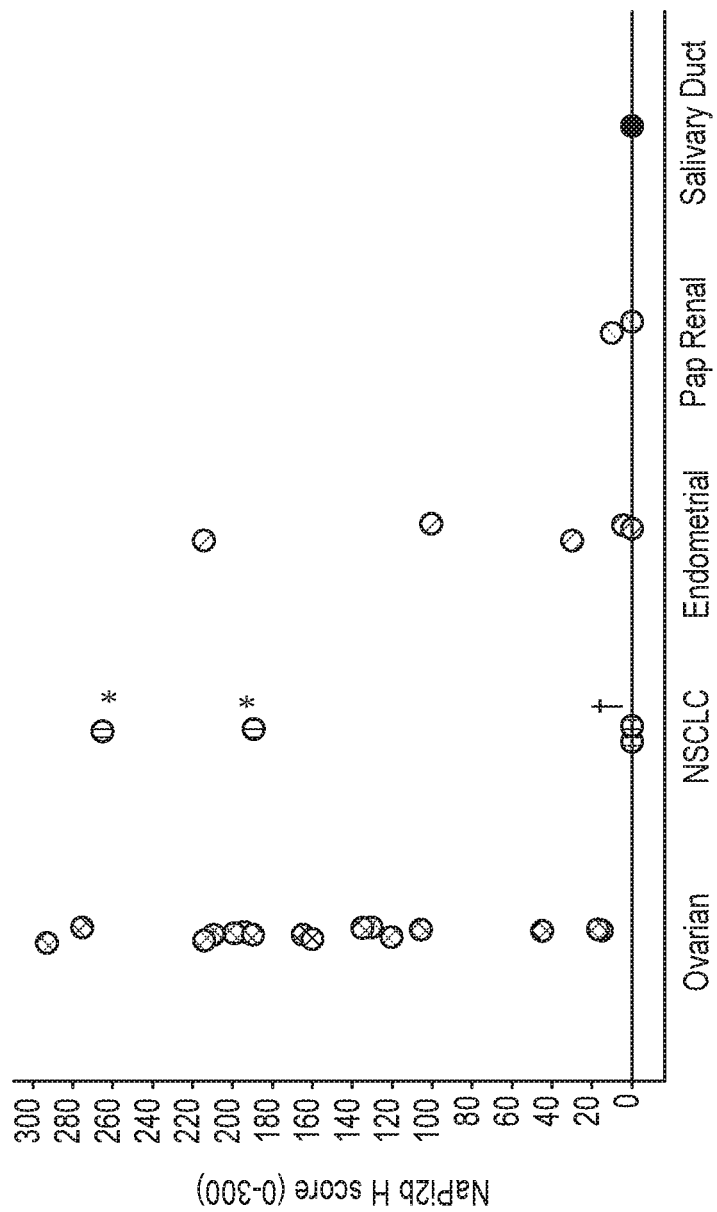
FIG. 6 shows the H-score obtained from NaPi2b protein expression by IHC from 34 patient tumor samples. The y axis shows the NaPi2b H-score and the x axis shows the tumor type.

FIG. 6 shows the NaPi2b protein expression in 34 patient tumor types e.g., ovarian, NSCLC, endometrial, papillary renal and salivary duct) wherein the fallopian tube and primary peritoneal tumor types are combined with the ovarian tumor types. The y axes is the H score in the range 0-300 for the number of positive tumor cells and staining intensity in NaPi2b IHC assay. Detectable NaPi2b protein expression was observed in all ovarian and lung adenocarcinoma samples.

Figure 7:
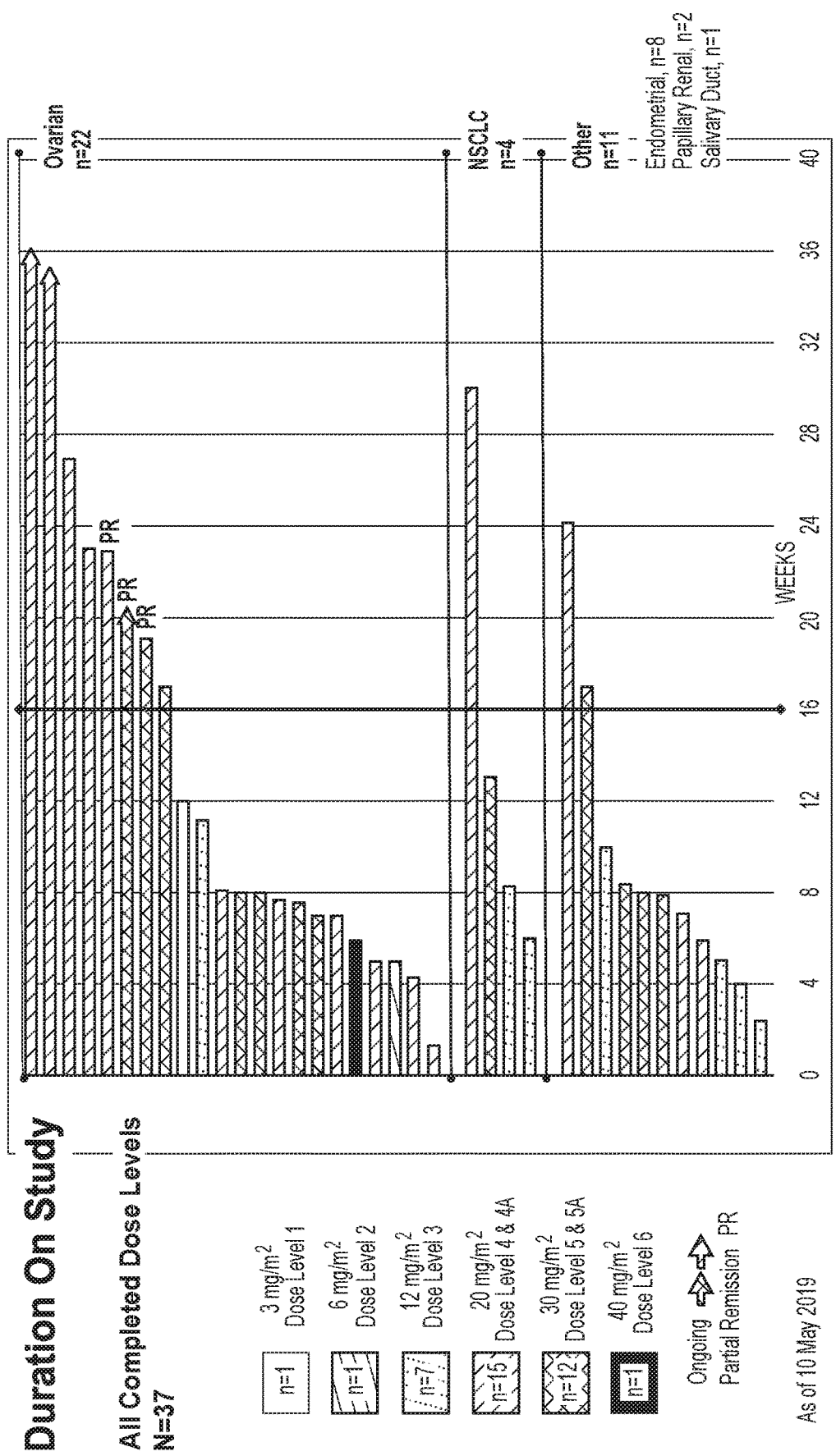
FIG. 7 is a "swimmers plot" that summarizes the details for the time on study for patients though DL6, 2-day cycle (n=20) and DL 4A and DL 5A patients dosed in the 28-day cycle (n=17).

FIG. 7 is a "swimmers plot" that summarizes the details for the time on study for patients though DL6, 21-day cycle (n=20) and DL 4A and DL 5A patients dosed in the 28-day cycle (n=17). The plot maps patients by dose level and tumor type on the y axis, against time on study drug on the x axis. The x axis is organized by week time intervals. At lower doses the majority of patients came off study because of progressive disease, but starting at DL4, most patients had stable disease.

Table 11 summarizes the reason for discontinuation participation in the study across the dose levels. Table 12 gives the outcome response for the evaluable population. Based on objective responses and duration of treatment, clinical activity was observed at doses of 20 mg/m$^2$ or higher.

TABLE 11

|  | DL1 3 mg/m$^2$ n = 1 | DL2 6 mg/m$^2$ n = 1 | DL3 12 mg/m$^2$ n = 7 | DL4 & 4A 20 mg/m$^2$ n = 13 | DL5 & 5A 30 mg/m$^2$ n = 11 | DL6 40 mg/m$^2$ n = 1 | Total n = 34[b] |
|---|---|---|---|---|---|---|---|
| Progressive Disease per RECIST | 1 | 1 | 3 | 7 | 6 |  | 18 (53%) |
| Clinical Progression[a] |  |  | 4 | 2 | 3 |  | 9 (26%) |
| Patient Choice |  |  |  | 2 | 1 | 1 | 4 (12%) |
| Physician Choice |  |  |  | 2 | 1 |  | 3 (9%) |

[a]Death in 3 of 10 patients, none related to XMT-1536
[b]3 patients are ongoing

TABLE 12

| Outcome | All Ovarian Cancer (OC) | All NSCLC | OC ≥ 20 mg/m$^2$ | NSCLC ≥ 20 mg/m$^2$ | OC + NSCLC ≥ 20 mg/m$^2$ | OC ≥ 30 mg/m$^2$ |
|---|---|---|---|---|---|---|
| N | 19 | 3 | 16 | 2 | 18 | 7 |
| PR* | 3 (16%) | 0 (0%) | 3 (19%) | 0 (0%) | 3 (17%) | 2 (28%) |

TABLE 12-continued

| Outcome | All Ovarian Cancer (OC) | All NSCLC | OC ≥ 20 mg/m² | NSCLC ≥ 20 mg/m² | OC + NSCLC ≥ 20 mg/m² | OC ≥ 30 mg/m² |
|---|---|---|---|---|---|---|
| SD* | 8 (42%) | 2 (67%) | 6 (38%) | 2 (100%) | 8 (44%) | 3 (43%) |
| DCR (PR + SD) | 11 (58%) | 2 (67%) | 9 (57%) | 2 (100%) | 11 (61%) | 5 (71%) |
| Treatment duration >16 weeks | 8 (42%) | 1 (33%) | 9 (57%) | 1 (50%) | 10 (56%) | 3 (43%) |
| PD* | 8 (42%) | 1 (33%) | 7 (43%) | 0 (0%) | 7 (39%) | 2 (28%) |

*As measured by RECIST, version 1.1

A 70-year-old woman with platinum-resistant high-grade serous ovarian cancer and 11 prior lines of therapy was treated at DL4A (20 mg/m²). Target lesions of perihepatic and mid-abdominal metastases, 52 and 42 mm respectively, decrease 40% in diameter at the end of Cycle 2 (4-week cycles) and 75% at the end of Cycle 3. Objective responses have been observed at doses of 20 mg/m² and higher. In ovarian cancer and lung adenocarcinoma patients treated at ≥20 mg/m² (N=18), 3 (17%) PRs and 8 (44%) SDs have been observed (ORR 17%, SD 44%, DCR 61%), with treatment duration of >16 weeks in 9 patients (50%) at doses of 20 mg/m² and higher (n=18).

Table 13 gives the characterization of the patients enrolled across 7 dose levels (2 to 40 mg/m), 21-day cycle and 3 dose levels 20 to 36 mg/m²), 28-day cycle as of August 2019.

TABLE 13

| Dose Level | Dose (mg/m²) | Cycle Durations (Days) | Tumor Types N | Age Range Y/o | Duration on Study Min/Max |
|---|---|---|---|---|---|
| 1 | 3 | 21 | N = 1 Ovarian | 55 | 4 cycles |
| 2 | 6 | 21 | N = 1 Ovarian | 54 | 2 cycles |
| 3 | 12 | 21 | N = 7 Ovarian-1 NSCLC- 2 Endometrial- 3 Papillary Renal- 1 | 39 to 67 Mean = 54 Median = 70 | 1 to 4 cycles |
| 4 | 20 | 21 | N = 6 Ovarian-2 NSCLC- 1 Endometrial- 1 Fallopian Tube- 1 Salivary Duct- 1 | 58 to 94 Mean = 72 Median = 70 | 1 to 10 cycles |
| 5 | 30 | 21 | N = 4 Ovarian- 3 NSCLC - 1 | 63 to 68 Mean = 66 Median = 66 | 1 to 4 cycles |
| 6 | 40 | 21 | N = 1 Ovarian Enrollment Complete | 54 | 1 cycle |
| 4A | 20 | 28 | N = 8 Ovarian N = 1 Papillary Renal | 47-74 Mean = 62 Median = 63 | 1 to 12 cycles |
| 5A | 30 | 28 | N = 8 Ovarian - 4 Endometrial - 4 | 51-76 Mean = 68 Median = 71 | 2 to 6 cycles |
| 5A Additional | 30 | 28 | N = 7 Ovarian - 6 NSCLC - 1 | 51-85 Mean = 68 Median = 71 | 2 cycles |
| 6A | | 28 | N = 7 Ovarian - 5 NSCLC - 2 | 47-63 Mean = 54 Median = 56 | 2 cycles |

The protocol was amended in July 2019. Eligibility criteria for enrolling ovarian cancer patients and non-small lung cancer patients were added. Table 14 is a summary of the patients dosed as of August 2019.

TABLE 14

| Dose Level (DL) | Dosing Regimen | Number of Patients |
|---|---|---|
| DL 1, 3 mg/m² | 21-day cycle, DLT observation period 1 cycle | 1 |
| DL 2, 6 mg/m² | 21-day cycle, DLT observation period 1 cycle | 1 |
| DL 3, 12 mg/m² | 21-day cycle, DLT observation period 1 cycle | 7 |
| DL 4, 20 mg/m² | 21-day cycle, DLT observation period 1 cycle | 6 |
| DL 5, 30 mg/m² | 21-day cycle, DLT observation period 1 cycle | 4 |
| DL 6, 40 mg/m² | 21-day cycle, DLT observation period 1 cycle | 1 |
| DL 4A, 20 mg/m² | 28-day cycle, DLT observation period 2 cycle | 9 |
| DL 5 A, 30 mg/m² | 28-day cycle, DLT observation period 2 cycle | 8 |
| DL 5 A, 30 mg/m² additional | 28-day cycle, DLT observation period 2 cycle | 7 |
| DL 6 A, 36 mg/m² | 28-day cycle, DLT observation period 2 cycle | 7 |

Figure 8:
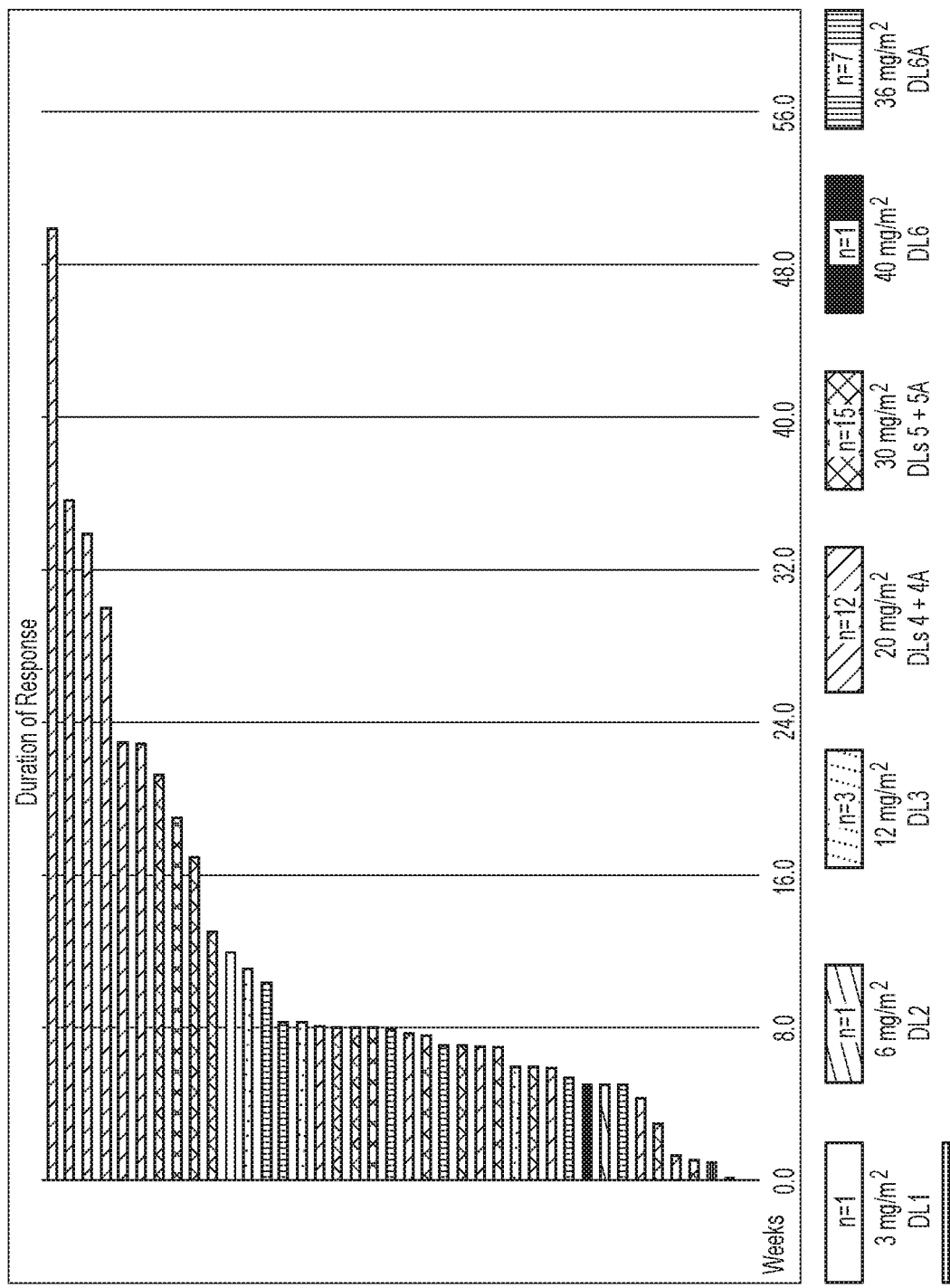
FIG. 8 is a "swimmers plot" that summarizes the details for the time on study for patients across 7 dose levels (2 to 40 mg/m$^2$), 21-day cycle and 3 dose levels (20 to 36 mg/m$^2$), 28-day cycle.

FIG. 8 is a "swimmers plot" that summarizes the details for the time on study for patients across 7 dose levels (2 to 40 mg/m²), 21-day cycle and 3 dose levels (20 to 36 mg/m²), 28-day cycle. The plot maps patients by dose level and tumor type on the y axis, against time on study drug on the x axis. The x axis is organized by week time intervals. At lower doses the majority of patients came off study because of progressive disease, but starting at DL4, most patients had stable disease. Maximum duration on study for a patient ongoing in the trial is 50 weeks.

CONCLUSIONS

XMT-1536 has been well-tolerated up to the 30 mg/m² or 36 mg/m² or 43 mg/m² dose level with early signs of anti-tumor activity. Neither MTD nor RP2D has been identified. Dose escalation continues in patients with NaPi2b-expressing ovarian cancer, NSCLC, papillary thyroid cancer, endometrial cancer, papillary renal cell cancer and salivary duct cancer

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a NaPi2b expressing tumor in a human subject in need thereof, the method comprising administering to the subject a NaPi2b-targeted antibody polymer-drug conjugate by infusion at a dose of about 36 mg/m² or about 43 mg/m² on the first day of treatment and every four weeks thereafter, wherein the conjugate comprises a NaPi2b antibody comprising: a CDRH1 comprising the amino acid sequence GYTFTGYNIH (SEQ ID NO: 5); a CDRH2 comprising the amino acid sequence AIYPGNGDT-SYKQKFRG (SEQ ID NO: 6); a CDRH3 comprising the amino acid sequence GETARATFAY (SEQ ID NO: 7); a CDRL1 comprising the amino acid sequence SASQDIGNFLN (SEQ ID NO: 8); a CDRL2 comprising the amino acid sequence YTSSLYS (SEQ ID NO: 9); and a CDRL3 comprising the amino acid sequence QQYSKLPLT (SEQ ID NO: 10); and a polymer-drug conjugate of Formula A:

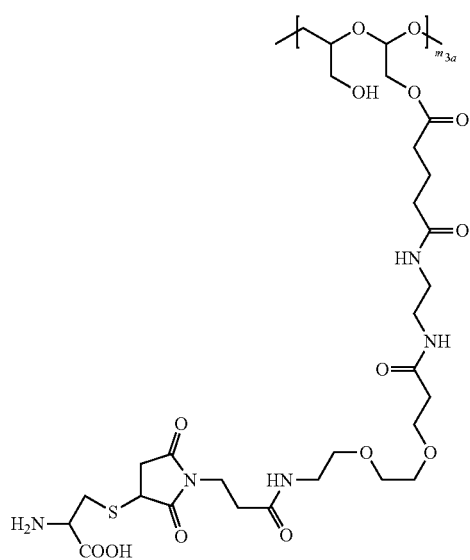

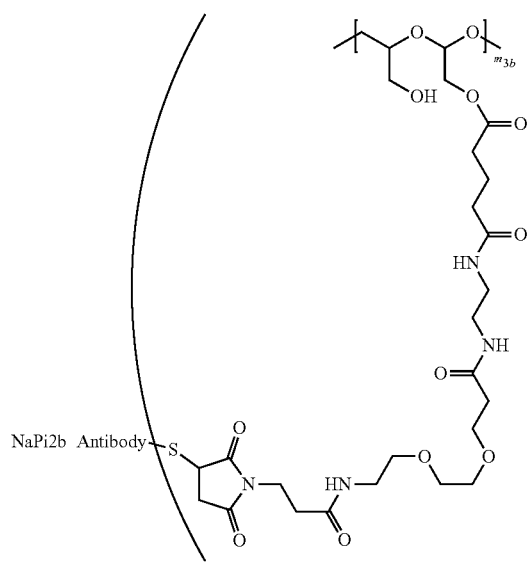

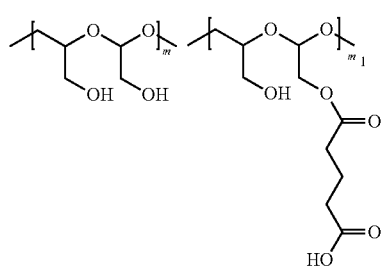

wherein:
the polymer comprises poly(1-hydroxymethylethylene hydroxymethyl-formal) (PHF) having a molecular weight ranging from about 5 kDa to about 10 kDa;
m is an integer from 20 to 75,
$m_1$ is an integer from about 5 to about 35,
$m_2$ is an integer from about 3 to about 10, $m_{3a}$ is an integer from 0 to about 4, $m_{3b}$ is an integer from 1 to about 5, the sum of m, $m_1$, $m_2$, $m_{3a}$, and $m_{3b}$ ranges from about 40 to about 75, and $m_5$ is an integer from about 2 to about 5;

wherein the tumor is selected from the group consisting of ovarian cancer, endometrial cancer, and non-small cell lung cancer (NSCLC).

2. The method of claim 1, wherein the NaPi2b antibody comprises a variable heavy chain comprising the amino acid sequence of SEQ ID NO: 3 and a variable light chain comprising the amino acid sequence of SEQ ID NO: 4; and a heavy chain comprising the amino acid sequence of SEQ ID NO: 1 and a light chain comprising the amino acid sequence of SEQ ID NO: 2.

3. The method of claim 1, wherein the ovarian cancer is epithelial ovarian cancer, fallopian tube cancer, or primary peritoneal cancer.

4. The method of claim 3, wherein the epithelial ovarian cancer is subtyped as high-grade serous ovarian cancer, low-grade ovarian cancer or clear cell ovarian cancer.

5. The method of claim 1, wherein the ovarian cancer is platinum resistant and the subject has received no more than 3 line of prior therapy.

6. The method of claim 1, wherein the subject has ovarian cancer and has received no more than 3 line of prior therapy.

7. The method of claim 1, wherein the NSCLC cancer is non-squamous and is sub-typed as adenocarcinoma.

8. The method of claim 7, wherein the subject has NSCLC and has received prior treatment with a platinum-based regimen and a PD-1 or PD-L1 monoclonal antibody.

9. The method of claim 8, wherein the platinum-based regimen and PD-1 or PD-L1 monoclonal antibody are administered in combination.

10. The method of claim 8, wherein the platinum-based regimen and PD-1 or PD-L1 monoclonal antibody are administered sequentially.

11. The method of claim 7, wherein the subject has received no treatment with a cytotoxic agent or has received no immunotherapy treatment.

12. The method of claim 1, wherein the endometrial cancer is epithelial endometrial cancer and is not a stromal tumor or a carcinosarcoma.

* * * * *